US010052390B2

(12) United States Patent
Lin et al.

(10) Patent No.: US 10,052,390 B2
(45) Date of Patent: Aug. 21, 2018

(54) IMMUNOSTIMULATORY NANOCOMPLEX

(71) Applicant: NATIONAL CHENG KUNG UNIVERSITY, Tainan (TW)

(72) Inventors: Yee-Shin Lin, Tainan (TW); Yu-Hung Chen, Tainan (TW)

(73) Assignee: National Cheng Kung University, Tainan (TW)

( * ) Notice: Subject to any disclaimer, the term of this patent is extended or adjusted under 35 U.S.C. 154(b) by 3 days.

(21) Appl. No.: 15/206,329

(22) Filed: Jul. 11, 2016

(65) Prior Publication Data

US 2017/0128593 A1 May 11, 2017

Related U.S. Application Data

(63) Continuation-in-part of application No. 13/924,793, filed on Jun. 24, 2013.

(30) Foreign Application Priority Data

Jan. 9, 2013 (TW) .............................. 102100790 A

(51) Int. Cl.
A61K 39/12 (2006.01)
C12N 7/00 (2006.01)
A61K 47/48 (2006.01)
A61K 39/00 (2006.01)

(52) U.S. Cl.
CPC ........ *A61K 47/48923* (2013.01); *A61K 39/12* (2013.01); *A61K 47/48907* (2013.01); *C12N 7/00* (2013.01); A61K 2039/55511 (2013.01); A61K 2039/55555 (2013.01); A61K 2039/55583 (2013.01); A61K 2039/622 (2013.01); A61K 2039/64 (2013.01); C12N 2770/24134 (2013.01)

(58) Field of Classification Search
None
See application file for complete search history.

(56) References Cited

U.S. PATENT DOCUMENTS

| 7,993,625 B1* | 8/2011 | Sung | A61K 47/6939 424/1.69 |
| 2012/0070454 A1* | 3/2012 | Lin | A61K 39/12 424/186.1 |
| 2014/0193446 A1* | 7/2014 | Lin | A61K 47/48923 424/186.1 |

* cited by examiner

Primary Examiner — Stacy B Chen
(74) Attorney, Agent, or Firm — Liang Legal Group, PLLC

(57) ABSTRACT

The present invention relates to an immunostimulatory nanocomplex. The immunostimulatory nanocomplex comprises polyglutamic acid (PGA), a first positively charged substance, a second positively charged substance and a dengue viral protein for holding the dengue viral protein inside. The immunostimulatory nanocomplex is characterized by having a nonuniformally and positively charge distribution along a radial direction thereof. The nonuniformally and positively charge distribution comprises a first electrically charged portion having substantially electrical neutrality, a second electrically charged portion surrounding the first electrically charged portion, and a third electrically charged portion surrounding the second electrically charged portion. The third electrically charged portion has a third volume charge density more than a second volume charge density of the second electrically charged portion, thereby enhancing CD8(+) T-cell response and higher antibody titer after administrating an organism with the immunostimulatory nanocomplex.

5 Claims, 30 Drawing Sheets
(14 of 30 Drawing Sheet(s) Filed in Color)

IMMUNOSTIMULATORY NANOCOMPLEX

RELATED APPLICATIONS

This application is a continuation-in-part of U.S. application Ser. No. 13/924,793, filed Jun. 24, 2013 now abandoned, which claims priority of Taiwan Application Serial Number 102100790, filed on Jan. 9, 2013, the entirety of which is incorporated by reference herein.

BACKGROUND

Field of Invention

The present invention relates to a nanocomplex. More particularly, the present invention relates to an immunostimulatory nanocomplex with electric property holds a dengue viral protein inside for inducing immune responses efficiently.

Description of Related Art

Dengue fever, also known as breakbone fever, is an acute viral disease transmitted by *Aedes aegypti* or *Aedes albopictus*, and its symptoms include fever (39° C.-40° C.) or aversion to cold, skin rash with fatigue in limb, muscle pains, frontal headache, orbital pain, abdominal pain, backache (i.e. the origin of the term "breakbone fever"), sore throat, and maybe vomiting, fainting, etc. The commonly mentioned dengue fever is classic dengue fever, also called as primary dengue fever. In addition, severe and life-threatening dengue fever characterized by hemorrhage or shock may be developed, also called dengue hemorrhagic fever (DHF) or dengue shock syndrome (DSS), or secondary dengue fever. It is estimated that there are about 50 million to 100 million cases of dengue infection worldwide each year, with about 250,000 to 500,000 cases of dengue hemorrhagic fever. Hence, the prevention and treatment of dengue fever is an important issue for the governments of many countries. Since dengue virus is the major pathogen of dengue disease, the early detection or prevention with effective vaccine can efficiently control morbidity and death rates of dengue fever.

Please refer to the Taiwan Patent Publication No. 201210614 and its corresponding U.S. patent Ser. No. 13/230,273 "Dengue vaccine, medicinal composition comprising the same, and nucleotide sequence", and the Taiwan Patent Publication No. 201210615 and its corresponding U.S. patent Ser. No. 13/230,209 "Dengue vaccine, medicinal composition comprising the same, nucleotide sequence, and antibody composition", which are applied by the inventors of the present invention. Taiwan Patent Publication No. 201210614 and its corresponding U.S. patent Ser. No. 13/230,273, and Taiwan Patent Publication No. 201210615 and its corresponding U.S. patent Ser. No. 13/230,209 are incorporated herein by reference. A dengue vaccine causing no autoimmunity to avoid the cross-reaction between endothelial cell and platelets and being able to shorten the bleeding time is disclosed in the foregoing applications, the contents of which are hereby incorporated by reference herein. The foregoing dengue vaccine has prospective effect in actual operation, but there is deficiency due to the aluminum hydroxide gel (also called as immunostimulant) as an adjuvant in the foregoing dengue vaccine. The ability of the aluminum hydroxide is undesired to enhance the immune response in the organism.

Commonly, the adjuvant action mechanism generally comprises: (a) increasing the life or the immunity of an antigen in the vaccine, (b) delivering antigen to the antigen-presenting cell, (c) improving antigen display in antigen-presenting cell, and (d) inducing the production of immunoregulatory cytokine. The mineral adjuvant is one of the common adjuvant, such as metal salts of zinc, calcium, cerium, chromium, iron, and beryllium. The aluminum salts, such as aluminum hydroxide and aluminum phosphate, is the most commonly used, and is also called as Alum adjuvant. The mechanism of the Alum adjuvant refers to the antigen being absorbed on the aluminum salt, which is also used as the immunostimulant, and when the antigen is taken up by antigen-presenting cell, the immunostimulant absorbed by the antigen stimulates the antigen-presenting cell at the same time.

Please refer to the U.S. Pat. No. 7,357,963, which is incorporated herein by reference. It disclosed a process for the manufacture of a vaccine, in which an adjuvant composition containing an immunostimulant adsorbed onto a first metallic salt particle substantially free of antigen is mixed with an antigen adsorbed onto a second metallic salt particle. The antigen is derived from human immunodeficiency virus, varicella zoster virus, human cytomegalovirus, dengue virus, hepatitis A, B, C or E virus. Actually, the Alum adjuvant is applied to over 50% of the commercial vaccine product, including hepatitis B vaccine (Alum-HBsAg), diphtheria and tetanus toxoid vaccine (Alum-DT), etc. The foregoing antigen-metal complex vaccine is used for years and it is proved that the complex is absorbed easily by the antigen-presenting cell, but it is doubted that the safety of the heavy metal. Accordingly, the safety adjuvant used in the vaccine application should be developed to avoid the unsafe problems resulting from the Alum adjuvant and to enhance the antibody production for better immune responses and lowering the administration frequency and the cost.

SUMMARY

In view of the foregoing disadvantages of the traditional dengue vaccine in actual operation, an aspect of the present invention is to provide an immunogenic composition with electric property holding a dengue viral protein inside. After administration with an immunostimulatory nanocomplex twice, an organism has higher antibody responses, the antibody production and CD8(+) T-cell response, so that the immunostimulatory nanocomplex induces the immune responses efficiently.

Moreover, another aspect of the present invention provides a method for making a biodegradable nanocomplex, in which zeta potentials of a first biodegradable macromolecule, a second biodegradable macromolecule and a dengue viral protein are measured, and then according to a charge ratio of the first biodegradable macromolecule to the second biodegradable macromolecule and a desired particle size of a secondary biodegradable carrier, a desired biodegradable nanocomplex with the adjustable zeta potential and the desired particle size is produced.

Furthermore, an other aspect of the present invention provides a vaccine composition, which comprises a biodegradable nanocomplex and at least one pharmaceutically acceptable excipient, and the biodegradable nanocomplex is made from an immunogenic composition as aforementioned or an addition salt thereof with a pharmaceutically acceptable base.

According to the aforementioned aspect, the invention provides an immunogenic composition, which comprises a biodegradable nanocomplex with electric property holding a dengue viral protein inside. After administration with the immunostimulatory nanocomplex twice, an organism has higher antibody responses. In comparison with the Alum adjuvant and Ribi adjuvant used in the traditional dengue vaccine of the prior art, the administration frequency of the immunostimulatory nanocomplex in the present invention is decreased to reduce the administration cost, so the immunostimulatory nanocomplex is good for being a commercial vaccine candidate. In addition, because of the biodegradability of the nanocomplex, the immunostimulatory nanocomplex is decomposed, absorbed and removed easily and naturally by the human body after it enters the human body. It resolves the unsafe problem resulting from the heavy metal of the Alum adjuvant, and the dengue viral protein held in the biodegradable nanocomplex is released slowly for the sustained release.

According to an embodiment of the present invention, the dengue viral protein comprises a nonstructural chimeric protein DJ NS1. The nonstructural chimeric protein DJ NS1 comprises N-terminal $1^{st}$ to $270^{th}$ amino acid of a dengue virus nonstructural protein (DV NS1) and C-terminal amino acid 271-352 of a Japanese encephalitis virus nonstructural protein (JEV NS1). Moreover, the nonstructural chimeric protein DJ NS1 has more than 90%, even more than 95%, sequence similarity to the SEQ ID NO: 1. Alternatively, the nonstructural chimeric protein DJ NS1ΔC comprises only N-terminal amino acid 1-270 of DV NS1 of the DV NS1, and the nonstructural chimeric protein DJ NS1ΔC has more than 90%, even more than 95%, sequence similarity to the SEQ ID NO: 2.

According to another embodiment of the present invention, the dose of the biodegradable nanocomplex is no more than 25 μg for the first administration. Moreover, when the immunostimulatory nanocomplex is made from the chitosan with positive charge and the polyglutamic acid with negative charge, after the second administration with the immunostimulatory nanocomplex, the organism has an antibody titer of 256000. Accordingly, in comparison with the prior art, the immunostimulatory nanocomplex of the present invention sharply increases the antibody production to induce the immune responses efficiently for enhancing the protection effect of the vaccine.

With application to the immunogenic composition, the method for making a biodegradable nanocomplex using the immunogenic composition, and the vaccine composition comprising the biodegradable nanocomplex, a desired biodegradable nanocomplex with the adjustable zeta potential and the desired particle size can be easily produced, for saving the testing numbers, obtaining the biodegradable nanocomplex with more uniform diameter and less standard deviation, and providing better administration effect to an organism.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows. The patent or application file contains at least one drawing executed in color. Copies of this patent or patent application publication with color drawing(s) will be provided by the Office upon request and payment of the necessary fee.

FIG. 3a is a FESEM image at 50,000-folded (×) magnification, in which the lower panel is depicted to an energy-dispersive x-ray spectroscopy (EDX) spectra of DJ NS1-encapsulated nanocomplexes, and the sulfur (S, k-electron line) signal represents the cysteines of the DJ NS1 protein. FIG. 3b is a FESEM image at 150,000× magnification, the lower panel is depicted to FESEM image of DJ NS1-encapsulated nanocomplexes with corresponding elemental mapping images of oxygen and sulfur in the selected area, indicating the homogeneous distribution of DJ NS1 protein in nanocomplexes. FIG. 3c is an analysis profile of the nanocomplex composition by FTIR, in which the peaks labeled with an asterisk represent the characteristic vibration modes from specific protein structures.

FIGS. 4a to 4c show results of cytotoxicity (FIG. 4a), histological examination (FIG. 4b) and enzyme activity of serum (FIG. 4c) of THP-1 cells treated with DJ NS1-encapsulated nanocomplexes or nanocomplexes alone in serial dilutions according to an embodiment of the present invention.

FIG. 6a is an experimental design of the DENV-induced mouse hemorrhagic model in C3H/HeN mice. FIG. 6b is a dot diagram of Groups of mice (n=10) subcutaneously immunized twice with 25 μg/mouse of DJ NS1 protein in nanocomplexes or alum. The bleeding time was determined at 3 days post-infection. $P<0.01$, *$P<0.001$, NS: not significant; one-way ANOVA with Tukey's post-test.

Figure 7A:
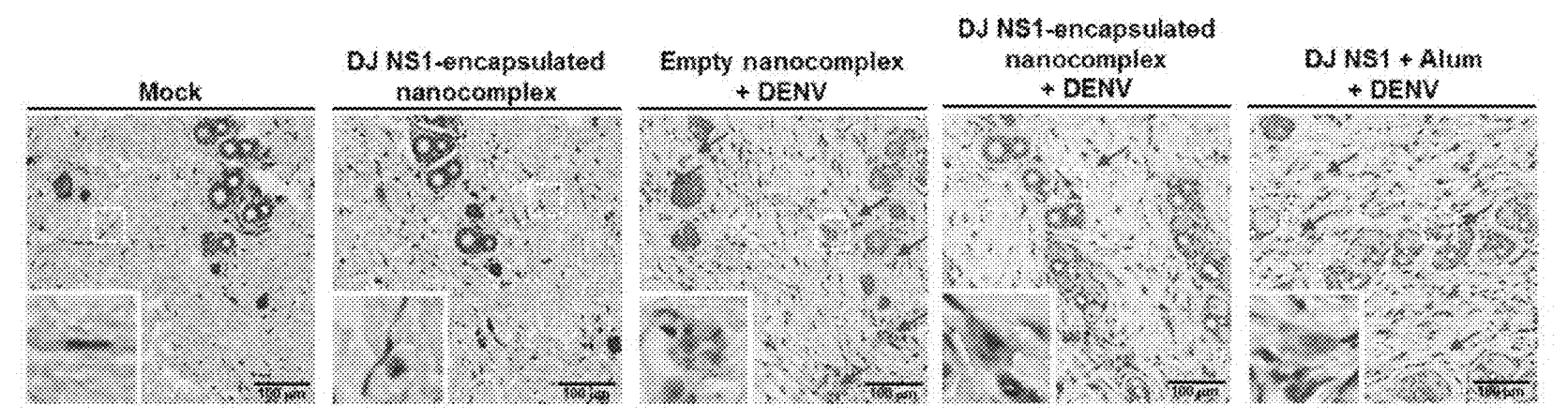

FIGS. 7a to 7b show active immunization results with DJ NS1-encapsulated nanocomplexes reduces DENV NS3 antigen expression at the skin inoculation site according to an embodiment of the present invention. The mice were intradermally inoculated with medium (Mock) or DENV2 16681 ($2 \times 10^8$ PFU/mouse) at four sites on the upper back and skin sections at the inoculation site were collected at 3 days post-infection. FIG. 7a show immunohistochemical (IHC) stainings of the local skin sections stained with anti-DENV NS3 Abs (red). Nuclei were stained with hematoxylin (blue). Red arrows indicate DENV NS3 antigen positive cells (Magnification: 200×). FIG. 7b is dot diagrams of DENV NS3 antigen positive cells counted in 15 regions per mouse field and the average numbers of NS3 positive cells calculated by HistoQuest software. *$P<0.05$, ***$P<0.001$, NS: not significant; one-way ANOVA with Tukey's post-test.

($2\times10^8$ PFU/mouse). The samples were collected at 3 days post-infection. FIG. 8a is a dot diagram of the concentrations of MCP-1 in mouse sera were measured by Cytometric Bead Array. FIG. 8b show IHC stainings of the local skin sections stained with anti-F4/80 Abs (red). Nuclei were stained with hematoxylin (blue). Red arrows indicate F4/80 positive cells (Magnification: 200×). FIG. 8c is dot diagrams of the F4/80 positive cells quantified in skin sections using HistoQuest analysis software. *$P<0.05$, $P<0.01$, *$P<0.001$, NS: not significant; one-way ANOVA with Tukey's post-test.

Figure 9C:
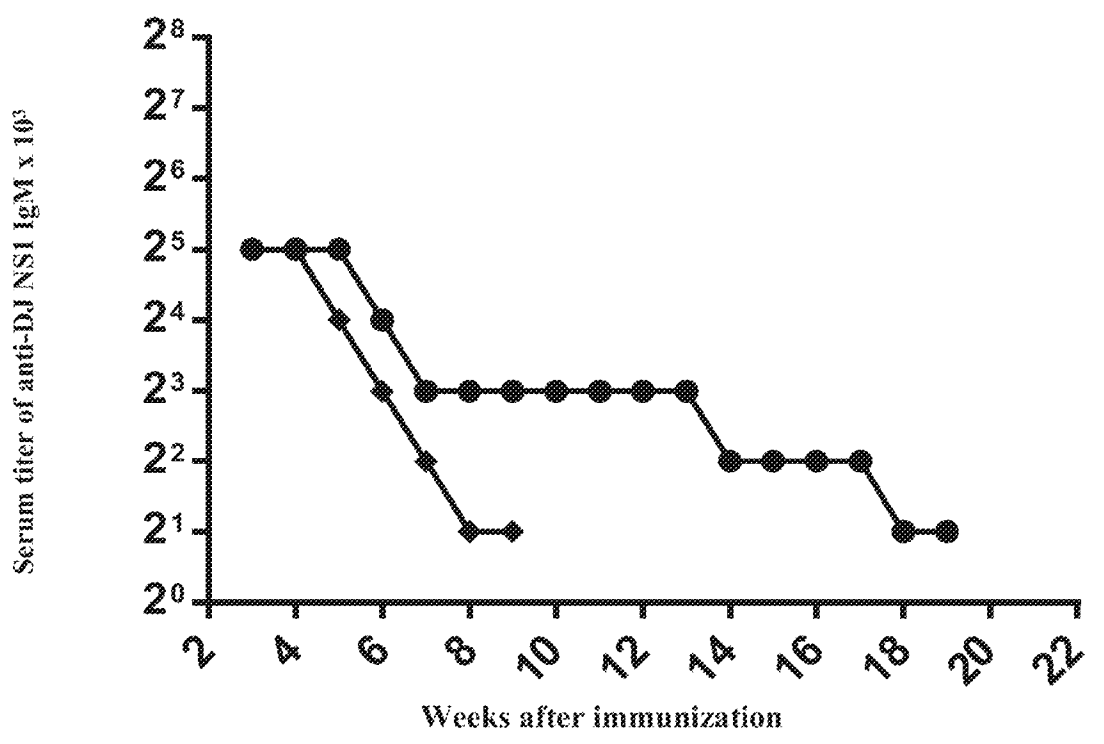

FIGS. 9a to 9d show DJ NS1 encapsulated nanocomplexes induce higher and longer-lasting DJ NS1-specific Ab responses than DJ NS1 with alum, and provide long-term protection. FIG. 9a is an experimental design of C3H/HeN mice subcutaneously immunized twice with 25 μg/mouse of DJ NS1 protein in nanocomplexes or alum. The DJ NS1-specific IgG (FIG. 9b) and IgM (FIG. 9c) titers in the sera from mice immunized with DJ NS1-encapsulated nanocomplexes or DJ NS1 plus alum were determined by ELISA. The dose of alum was 100 μg/mouse. FIG. 9d is a dot diagram of mice subsequently intradermally injected with medium (Mock) or DENV2 16681 ($2\times10^8$ PFU/mouse) at four sites on the upper back at 21 weeks after immunization. The bleeding time was determined at 3 days post-infection. (n=5/group) *$P<0.05$, ***$P<0.001$, NS: not significant; one-way ANOVA with Tukey's post-test.

Figure 10A:
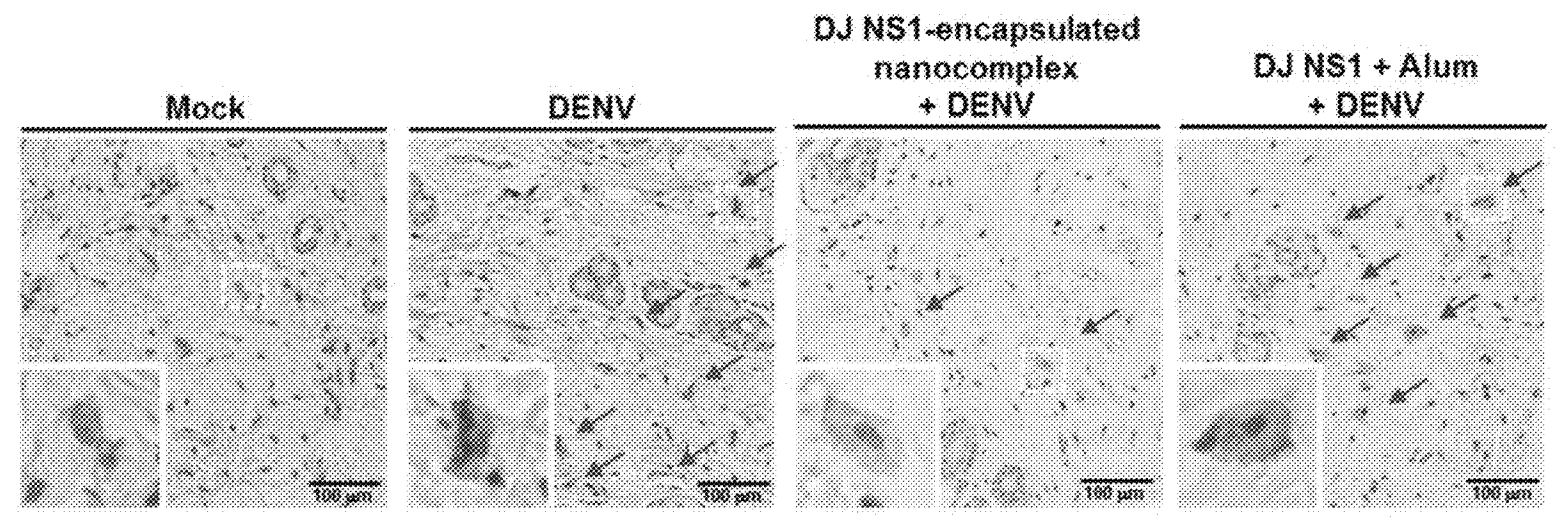

FIGS. 10a to 10d show active immunization results with DJ NS1-encapsulated nanocomplexes reduces DENV NS3 antigen expression and macrophage infiltration at the skin inoculation site in a long-term mouse model. The local skin sections at the virus inoculation site were fixed in paraffin, and stained with anti-DENV NS3 Abs (FIG. 10a) or anti-F4/80 Abs (FIG. 10c) (red). Nuclei were stained with hematoxylin (blue). Arrows indicate positive staining Magnification: 200×). The DENV NS3 antigen positive cells (FIG. 10b) or F4/80 positive cells (FIG. 10d) in skin sections were counted in 15 regions per mouse field and the average numbers of positive cells were further quantified using HistoQuest analysis software. *$P<0.05$, $P<0.01$, *$P<0.001$, NS: not significant; one-way ANOVA with Tukey's post-test.

DETAILED DESCRIPTION

Figure 1:
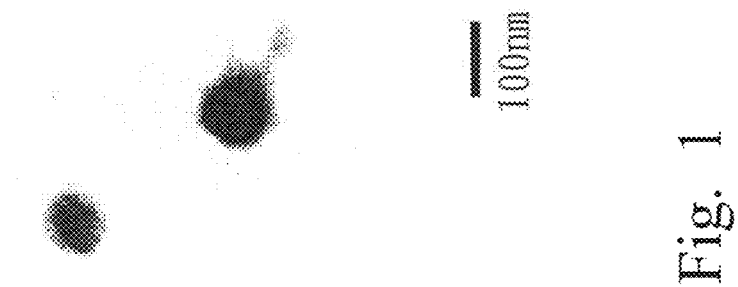
FIG. 1 is an electron microscope image of a biodegradable nanocomplex holding a dengue viral protein inside according to an embodiment of the present invention.

Hereinafter, various applications of the immunostimulatory nanocomplex will be described in more details referring to several exemplary embodiments below, while not intended to be limiting. Thus, one skilled in the art can easily ascertain the essential advantages and effects of the present invention and, without departing from the spirit and scope thereof, can make various changes and modifications of the invention to adapt it to various usages and conditions.

An immunostimulatory nanocomplex is disclosed, which comprises polyglutamic acid (PGA), a first positively charged substance, a second positively charged substance and a dengue viral protein for holding a dengue viral protein inside. In an embodiment, the dengue viral protein has a polypeptide sequence of SEQ ID NOs: 1 or 2. In some embodiments, the immunostimulatory nanocomplex characterized by having a nonuniformally and positively charge distribution along a radial direction thereof. The nonuniformally and positively charge distribution comprises a first electrically charged portion having a first volume charge density, a second electrically charged portion surrounding the first electrically charged portion, and a third electrically charged portion surrounding the second electrically charged portion. The first volume charge density is substantially neutral. The third electrically charged portion has a third volume charge density more than a second volume charge density of the second electrically charged portion, and the third electrically charged portion comprises an outermost surface of the immunostimulatory nanocomplex. After administration with the immunostimulatory nanocomplex, an organism has higher CD8(+) T-cell response and antibody responses.

It is noted that the foregoing dengue viral protein can be dengue envelope protein or dengue nonstructural protein. According to an embodiment of the present invention, the dengue viral protein of SEQ ID NO: 1 is disclosed in the U.S. Patent Publication No. 20120065373 "Dengue vaccine, medicinal composition comprising the same, and nucleotide sequence", the contents of which are hereby incorporated by reference herein. The dengue viral protein comprises a nonstructural chimeric protein DJ NS1. The nonstructural chimeric protein DJ NS1 comprises N-terminal amino acid 1-270 of a dengue virus nonstructural protein (DV NS1) and C-terminal amino acid 271-352 of a Japanese encephalitis virus nonstructural protein (JEV NS1). Moreover, the sequence similarity between the nonstructural chimeric protein DJ NS1 and the SEQ. ID. NO. 1 is more than 90%, even more than 95%. The dengue viral protein of SEQ ID NO: 2 is a nonstructural protein DJ NS1ΔC comprising N-terminal amino acid 1-270 of the dengue virus nonstructural protein.

In an embodiment, the immunostimulatory nanocomplex has a zeta potential of 10 mV to 35 mV. In a certain embodiment, the first positively charged substance and the second positively charged substance are the same or different. Suitable examples of the first positively charged substance and the second positively charged substance include but are not limited to chitosan (CS), gelatin, cationic cyclodextrin, cationic dextran, poly(L-lysine), polyethylenimine and polyamidoamine.

The method for making an immunostimulatory nanocomplex of the present invention can comprise the following steps. Zeta potentials of PGA, a first positively charged substance, a second positively charged substance and a dengue viral protein of SEQ. ID. NO. 1 can be measured respectively. And then, the dengue viral protein can be added into a first solution of the PGA, thereby forming a dispersion, wherein the γ-PGA and the dengue viral protein have the same electrical charge. Followingly, a zeta potential of the dispersion can be adjusted by adding the first positively charged substance into the dispersion, in which a difference of a zeta potential of the γ-PGA minus a zeta potential of the dengue viral protein plus a zeta potential of the first positively charged substance is more than 10 mV. If the difference of a zeta potential of the γ-PGA minus a zeta potential of the dengue viral protein plus a zeta potential of the first positively charged substance was less than 10 mV, the resultant immunostimulatory nanocommplex would not have the nonuniformally and positively charge distribution. Later, the second positively charged substance are added into the dispersion, thereby forming the immunostimulatory nanocomplex for holding the dengue viral protein inside, and the immunostimulatory nanocomplex has a nonuniformally and positively charge distribution along a radial direction thereof as aforementioned. The immunostimulatory nanocomplex can effectively enhance CD8(+) T-cell response and higher antibody titer after administrating an organism with the immunostimulatory nanocomplex.

Thereinafter, various applications of the immunostimulatory nanocomplex and the method for making the same will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

EXAMPLES OF PREPARATION

1. Preparation of Recombinant Chimeric DJ NS1 Proteins.

This procedure was followed as previously reported by Wan, S. W. et al. in *PLoS One* 9, e92495 (2014), the entirety of which was incorporated by reference herein. Briefly, DJ NS1 (a.a. 1-270 of DENV NS1 and a.a. 271-352 of JEV NS1) cDNA was cloned into the pET28a vector with histag. The plasmids were prepared by the Proteomic Research Core Facility, Academia *Sinica*. Following introduction of the plasmids into *Escherichia coli* BL21, the recombinant proteins were induced by 1 M isopropyl B-D-1-thiogalactopyranoside (IPTG) (Calbiochem), solubilized in urea buffer (8 M urea, 500 mM NaCl, and 20 mM Tris-HCl) and purified on a $Ni^{2+}$ column (GE Healthcare Life Science). After purification, proteins were examined using 10% sodium dodecyl sulfate polyacrylamide gel electrophoresis (SDS-PAGE), followed by staining with Coomassie brilliant blue R250. Purified proteins were dialyzed in refolding buffer (50 mM Tris-HCl, 50 mM NaCl, 2 mM reduced glutathione, 0.2 mM oxidized glutathione, 1 mM EDTA, and 0.1 mM PMSF) and concentrated by Amicon Ultra (Millipore).

2. Preparation and Characterization of DJ NS1-Encapsulated Polymer-Based Nanocomplexes.

A low-MW CS was obtained from the depolymerization of a commercially available CS. Given a low-MW, the polycationic CS has a good solubility at a pH value close to physiological range. CS (MW 280 kDa) with a degree of deacetylation of approximately 85% (Sigma-Aldrich, St. Louis, Mo., USA) was treated with sodium perborate tetrahydrate ($NaBO_3$, Sigma-Aldrich) to produce low-MW CS. A sample of 25 μg of DJ-NS1 protein was premixed with aqueous γ-PGA (1 mg/ml, 5 ml) and added into aqueous CS (6 mg/ml, 0.5 ml) under magnetic stirring in the 10 mM phosphate buffer (pH=6) at room temperature (approximately 4° C. to 40° C.). The samples were concentrated to 1/10 of volume and stored at 4° C. The particle size and zeta potential of the prepared nanoparticles were measured using a quasi-elastic light scattering (QELS) analyzer (3000HS, Malvern Instruments, Worcestershire, UK). FT-IR was recorded on a NEXUS 670 spectrometer equipped with a liquid nitrogen-cooled MCT detector by using the attenuated total reflectance (ATR) technique. The spectra were obtained by 1000 scans with a resolution of 1 $cm^{-1}$ over wavenumbers ranging from 650-4000 $cm^{-1}$ and data were processed using the Omnic software. FESEM analysis was performed on a HR-SEM electron microscope with an EDX spectrometer (JEOL JSM-6700F, Tokyo, Japan). To determine the loading content and loading efficiency, the DJ NS1-encapsulated nanocomplexes were collected by ultracentrifugation at 30,000 rpm, 4° C. for 60 min, and the free DJ NS1 protein concentration was analyzed in the supernatant by high-performance liquid chromatography (HPLC). The DJ NS1 loading content and loading efficiency of the nanocomplexes were determined as described in the literature and calculated from the following equations.

$$\text{loading content}(\%) = \frac{\text{total amount of } DJ\ NS1 - \text{amount of free } DJ\ NS1}{\text{weight of nanocomplex}} \times 100$$

$$\text{loading efficiency}(\%) = \frac{\text{total amount of } DJ\ NS1 - \text{amount of free } DJ\ NS1}{\text{total amount of } DJ\ NS1} \times 100$$

3. Mice.

C3H/HeN mice were obtained from National Laboratory Animal Center, Tainan facility and maintained on standard laboratory food and water in the Laboratory Animal Center of National Cheng Kung University Medical College. Their 6-week-old progeny were used for the experiments. Animal handling and procedures were reviewed and approved by the Institutional Animal Care and Use Committee (IACUC) of National Cheng Kung University, and conducted in accordance with the Guidelines for Committee of Laboratory Care and Use, National Cheng Kung University.

4. Cell Cultures.

Baby hamster kidney cells (BHK-21) and C6/36 cells were cultured in Dulbecco's modified Eagles medium (DMEM) (Invitrogen) containing antibiotics and 5% or 10% fetal bovine serum (FBS). Cells were detached using 1000 U/ml trypsin and 0.5 mM EDTA. Human monocytic THP-1 cells were grown in RPMI 1640 medium (Invitrogen) containing 2 mM L-glutamine, 1 mM sodium pyruvate and supplemented with 10% FBS.

5. Virus Culture.

DENV serotype 2 (strain 16681) was maintained in C6/36 cells. Briefly, monolayers of C6/36 cells were incubated with DENV at a multiplicity of infection (MOI) of 0.01 and incubated at 28° C. in 5% $CO_2$ for 5 days. The cultured medium was harvested and cell debris was removed by centrifugation at 1000×g for 10 min. The virus supernatant was collected and stored at −70° C. until use. Virus titer was determined by plaque assay using the BHK-21 cell line.

6. Mouse Immunization and Challenge.

DJ NS1 proteins were encapsulated into polymer-based nanocomplexes or emulsified with an equal volume of alum solution (Thermo). The preparations were tested for endotoxin level using ToxinSensor Chromogenic LAL Endotoxin Assay Kit (GenScript). The endotoxin levels were all <1 EU/ml. C3H/HeN mice were subcutaneously injected twice (with an interval of 14 days) with 25 μg/mouse DJ NS1 proteins in polymer-based nanocomplexes or alum. Three days or 21 weeks (for long-term protection model) following the final immunization, mice were intradermally injected with medium or DENV ($2\times10^8$ PFU/mouse) at four sites on the upper back and sacrificed at day 3 after inoculation.

7. Antibody Titer Determination.

DJ NS1 proteins were coated on 96-well plates at 0.2 mg/well in coating buffer ($NaCO_3$ 1.59 g, $NaHCO_3$ 2.93 g, pH 9.6, in 1 L ddH$_2$O) at 4° C. overnight. The plates were blocked with 1% bovine serum albumin (BSA) in PBS at 4° C. overnight, and then washed three times with 0.05% Tween 20 in PBS (PBS-T). Mouse sera were diluted serially from 1:1000 to 1:2048000. The diluted mouse sera were added into protein-coated wells, and incubated at 4° C. overnight. After washing three times, peroxidase-conjugated anti-mouse IgG or IgM was added into each well and incubated for 2 h at room temperature. After washing, ABTS (Sigma-Aldrich) was added into each well and the absorbance was measured at 405 nm.

8. Mouse Tail Bleeding Time.

Bleeding time was performed with a 3-mm tail-tip transaction. Blood droplets were collected on filter paper every 30 sec. Bleeding time was recorded when the blood spot was smaller than 0.1 mm in diameter.

9. Detection of Serum MCP-1 Levels.

The concentrations of serum MCP-1 were measured by a flow cytometry application with Cytometric Bead Array (CBA; BD Biosciences). Briefly, the standard mixtures were prepared by serial dilutions. Then, 50 ml of mouse sera or standards were incubated with 50 ml of prepared biotin-conjugated capture beads mixture for 1 h at room temperature. Then, 50 ml of prepared streptavidin-PE detection beads mixture were added for 1 h at room temperature. After washing twice with 1 ml of washing buffer, the beads were resuspended with 200 ml of assay buffer. The data were collected by flow cytometry and results were further analyzed by FCAP Array v3.0 Software (BD Biosciences).

10. Immunohistochemistry Staining.

The skin sections were embedded in paraffin and sliced on slides. Slides were deparaffinized using xylene and gradient alcohol (100%, 95%, 85%, 70% and 50%). The sections were then incubated in 2N HCl solution for 20 min followed by treatment with 20 mg/ml proteinase K in TE buffer (50 mM Tris Base, 1 mM EDTA, and 0.5% Triton X-100, pH 8.0) for another 20 min at room temperature. The sections were incubated with 3% H$_2$O$_2$ in PBS for 15 min to inhibit endogenous peroxidase activity and blocked by 5% BSA in PBS-T.

The primary and secondary Abs were adequately diluted in Ab diluents (Dako Corporation). The DENV antigen was stained with polyclonal anti-DENV NS3 Abs (GeneTex) overnight at 4° C., followed by biotin-labeled donkey anti-rabbit Abs at room temperature for 1 h. The infiltrating macrophages were stained by rat anti-mouse F4/80 Abs (AbD Serotec, clone CI:A3-1) overnight at 4° C., followed by biotin-labeled donkey anti-rat Abs (Jackson ImmunoResearch Laboratories) at room temperature for 2 h. After washing with PBS-T twice, the sections were incubated with HRP-conjugated streptavidin (Dako Corporation) for 15 min at room temperature. The skin sections were developed with the AEC substrate kit (Dako Corporation) and nuclei were further stained with hematoxylin (ScyTek Laboratories) for 10 sec. The positive cells were counted in 15 regions per mouse skin field and the average numbers of positive cells were calculated by HistoQuest software (TissueGnostics).

11. Statistical Analysis.

Data was expressed as the mean±SD. Multiple intergroup comparisons were assessed by one-way ANOVA, followed by post hoc Tukey's test with GraphPad Prism version 6.0. Statistical significance was set at $P<0.05$.

Example 1: Prepare a First Solution Comprising a First Biodegradable Macromolecule The first solution comprises a first biodegradable macromolecule with first electric property, and the first biodegradable macromolecule is polyglutamic acid (γ-PGA) or heparin and the first electric property is negative charge, for example. In detail, a proper amount of polyglutamic acid was added into de-ionized water and stirred by electromagnetic stirrer until the polyglutamic acid was totally dissolved. Then, the sodium in the polyglutamic acid solution was removed by membrane dialysis. The dialysis process was accomplished at 4° C. for preventing bacterial growth. After dialysis, the polyglutamic acid solution was put at −20° C. for being totally frozen. Then, the water content of the frozen polyglutamic acid solution was removed by lyophilization to obtain the crystallized powder of the polyglutamic acid. The crystallized powder of the polyglutamic acid was stored in a sterilized tube and put in a moisture-proof box. Finally, a proper amount of crystallized powder of the polyglutamic acid was taken and dissolved in the de-ionized water in a desired concentration, which was the first solution comprising the first biodegradable macromolecule with negative charge.

However, one skilled in the art will readily recognize that the foregoing method for preparation of the first solution is one of embodiments. After reading and understanding the descriptions of the present invention, it will be obvious to those skilled in the art that various modifications may be made and not limited to the foregoing embodiment.

Example 2: Prepare a Mixture Solution Containing a Dengue Viral Protein and the First Solution A dengue viral protein with the same electric property as the first biodegradable macromolecule was dissolved in the first solution to form a mixture solution with negative charge. The dengue viral protein was disclosed in the Taiwan Patent Publication No. 201210614 "Dengue vaccine, medicinal composition comprising the same, and nucleotide sequence." The dose of the dengue viral protein was 100 μg, 200 μg, or 400 μg, and it is not limited here.

Example 3: Prepare a Second Solution Comprising a Second Biodegradable Macromolecule A second solution comprising a second biodegradable macromolecule with a second electric property is prepared, and the first electric property is opposite to the second electric property. The second biodegradable macromolecule is chitosan or collagen, for example, and the second electric property is positive charge. In detail, the second biodegradable macromolecule was chitosan. 5 g low-viscous chitosan was added into 495 ml de-ionized water with 5 ml glacial acetic acid and stirred by electromagnetic stirrer until the chitosan solution stays in a yellow and pellucid state. Next, the glacial acetic acid in the chitosan solution was removed by membrane dialysis, and the pH of the chitosan solution was about 6.5 after dialysis. Then, the chitosan solution was filtrated by air suction filter to remove the impurity. Finally, the chitosan solution was heated and stirred at 135° C. for being concentrated until the concentration of the chitosan solution reaches 20-30 mg/ml, which was the second solution comprising the second biodegradable macromolecule with positive charge.

Similarly, one skilled in the art will readily recognize that the foregoing method of preparation of the second solution is one of embodiments. After reading and understanding the descriptions of the present invention, it will be obvious to those skilled in the art that various modifications may be made and not limited to the foregoing embodiment.

It is noted that the foregoing first and second biodegradable macromolecule can be natural macromolecules, such as heparin or polyglutamic acid, and chitosan or collgen, respectively. The foregoing first and second biodegradable macromolecule also can be artificially biodegradable macromolecules.

Example 4: Form a Biodegradable Nanocomplex

The mixture solution was added into the second solution to form a biodegradable nanocomplex by attraction force between the different electric properties, and the dengue viral protein was held in the biodegradable nanocomplex. FIG. 1 is an electron microscope image of a biodegradable nanocomplex holding a dengue viral protein inside according to an embodiment of the present invention. It is worth noted that the dengue viral protein with negative charge is mixed with the polyglutamic acid solution with negative charge to form a mixture solution first, and then the mixture solution is mixed with the chitosan solution with positive charge to form the biodegradable nanocomplex solution, in which the structure of the biodegradable nanocomplex is more stable. However, the dengue viral protein with negative charge also can be mixed with the chitosan solution with positive charge first to form a mixture solution, and then the mixture solution is mixed with the polyglutamic acid solution. Because of the biodegradability of the first and second macromolecule, the nanocomplex formed from the first and second macromolecule has biodegradability as well. The biodegradability means that the nanocomplex is decomposed, absorbed and removed easily and naturally by the human body after it enters the human body, and the dengue viral protein held in the nanocomplex is released slowly for the sustained release. Table 1 is the particle size and the zeta potential of the biodegradable nanocomplex with and without holding the dengue viral protein at various charge ratio of chitan to polyglutamic acid (CS/γ-pga). The results of the particle size and zeta potential are the average value of three biodegradable nanocomplexes.

TABLE 1

|  | without holding dengue viral protien | with holding dengue viral protein | | |
| --- | --- | --- | --- | --- |
|  |  | CS/γ-pga = 4:1 | CS/γ-pga = 6:1 | CS/γ-pga = 8:1 |
| Size (nm) | 126.4 ± 5.1 | 124.5 ± 1.8 | 130.5 ± 2.5 | 123.1 ± 1.7 |
| Zeta potential (mV) | 83.5 ± 6.2 | 15.4 ± 0.7 | 22.9 ± 0.8 | 31.1 ± 0.7 |

Example 5: Administration with the Immunostimulatory Nanocomplex Holding Dengue Viral Protein Inside on a Mouse Model Mice are vaccinated with the biodegradable nanocomplex holding the dengue viral protein inside as a model compound. C3H/HeN mice were obtained from the Jackson Laboratory, and maintained on standard laboratory food and water in the Laboratory Animal Center of National Cheng Kung University Medical College in Taiwan (R.O.C.). Housing, breeding, and experimental use of the animals were performed in strict accordance with the Experimental Animal Committee in the laboratory animal center of National Cheng Kung University. Table 2 is the results of a titer of a neutralizing antibody in the mice vaccinated by the biodegradable nanocomplex holding the dengue viral protein inside of the present invention, by the traditional Alum adjuvant, or by the traditional Ribi adjuvant.

TABLE 2

| | Antibody titer to the DJ NS1(×10³) | | | | | |
| --- | --- | --- | --- | --- | --- | --- |
| Administration | Nanocomplex (μg/mouse) | | Alum (μg/mouse) | | Ribi (μg/mouse) | |
| time | 25 | 50 | 25 | 50 | 25 | 50 |
| First | ND | ND | ND | ND | ND | ND |
| Second | $2^8$ | $2^9$ | ND | ND | ND | ND |
| Third | $2^{10}$ | $2^{11}$ | $2^6$ | $2^8$ | $2^7$ | $2^8$ |

According to Table 2, after administration twice, a specific antibody response was induced by the dengue vaccine comprising the biodegradable nanocomplex of the present invention, and the mice had the antibody titer of 256000 when the dose of the biodegradable nanocomplex in the dengue vaccine is 25 μg per administration. Accordingly, the administration times of the biodegradable high-efficiency dengue vaccine in the present invention is decreased, so the biodegradable high-efficiency dengue vaccine is good for being a commercial vaccine. The ND means that the antibody titer is non-detectable. The antibody titer was measured by an ELISA standard protocol. The time of antibody response induced by the biodegradable nanocomplex was faster than that induced by the traditional Alum adjuvant and Ribi adjuvant. In detail, the traditional Alum adjuvant and Ribi adjuvant induced the specific antibody response to the dengue viral protein in the mice until the third administration. Moreover, after the third administration, the antibody titer induced by the biodegradable nanocomplex of the present invention was higher than that induced by the foregoing Alum adjuvant and Ribi adjuvant. It is suggested that the biodegradable nanocomplex holding dengue viral protein inside enhanced the adjuvant effect in the dengue vaccine. The foregoing Ribi adjuvant was non-toxic and non-immunity oil-in-water emulsions in Ribi adjuvant system (RAS) developed by the Ribi Immunochem Research Inc. in 1985.

In the other embodiment of the present invention, the biodegradable nanocomplex made from heparin as the first biodegradable macromolecule and chitosan as the second biodegradable macromolecule also induced the specific antibody response to the dengue viral protein in mice after the second administration, and the dose of the biodegradable nanocomplex in the dengue vaccine is 25 μg per administration. The organism had the antibody titer of 32000 at least after the second administration.

A pharmaceutical composition comprising the dengue vaccine comprising the foregoing biodegradable nanocomplex is also provided, which is used for producing a vaccine or a drug for treating or preventing hemorrhagic dengue fever or dengue shock syndrome. The pharmaceutical composition comprises the foregoing biodegradable high-efficiency dengue vaccine or an addition salts thereof with a pharmaceutically acceptable base, and at least one pharmaceutically acceptable excipient. Moreover, the pharmaceutical composition of the present invention can be administered to animals in any existing ways, i.e. oral, nasal, mucosal, topical, dermal, and parenteral administration, wherein parenteral administration is intravenous, intraperitoneal, intradermal, subcutaneous, or intramuscular administration. The pharmaceutical composition of the present invention also can be administered via the combination of the foregoing administrations. For example, the first administration is via parenteral administration, and the second administration is via mucosal administration. In addition, the dose of the pharmaceutical composition varies depending on the species, age, weight, and status of individuals, the disease to be prevented or treated, the seriousness of the disease, the specific compound use in the pharmaceutical composition, and administration methods. One skilled in the art will readily recognize the publication content of the present invention, a proper dose can be decided by the routine experiment, and after the first administration, the organism can be decided to receive one or more additional administrations at a proper interval.

Hereinafter, there are several reasons why the present invention emphasizes "the charge ratio of the second biodegradable macromolecule to the first biodegradable macromolecule" and "the biodegradable nanocomplex made from the immunogenic composition has positive charge for holding the dengue viral protein inside".

Example 6

Figure 2:
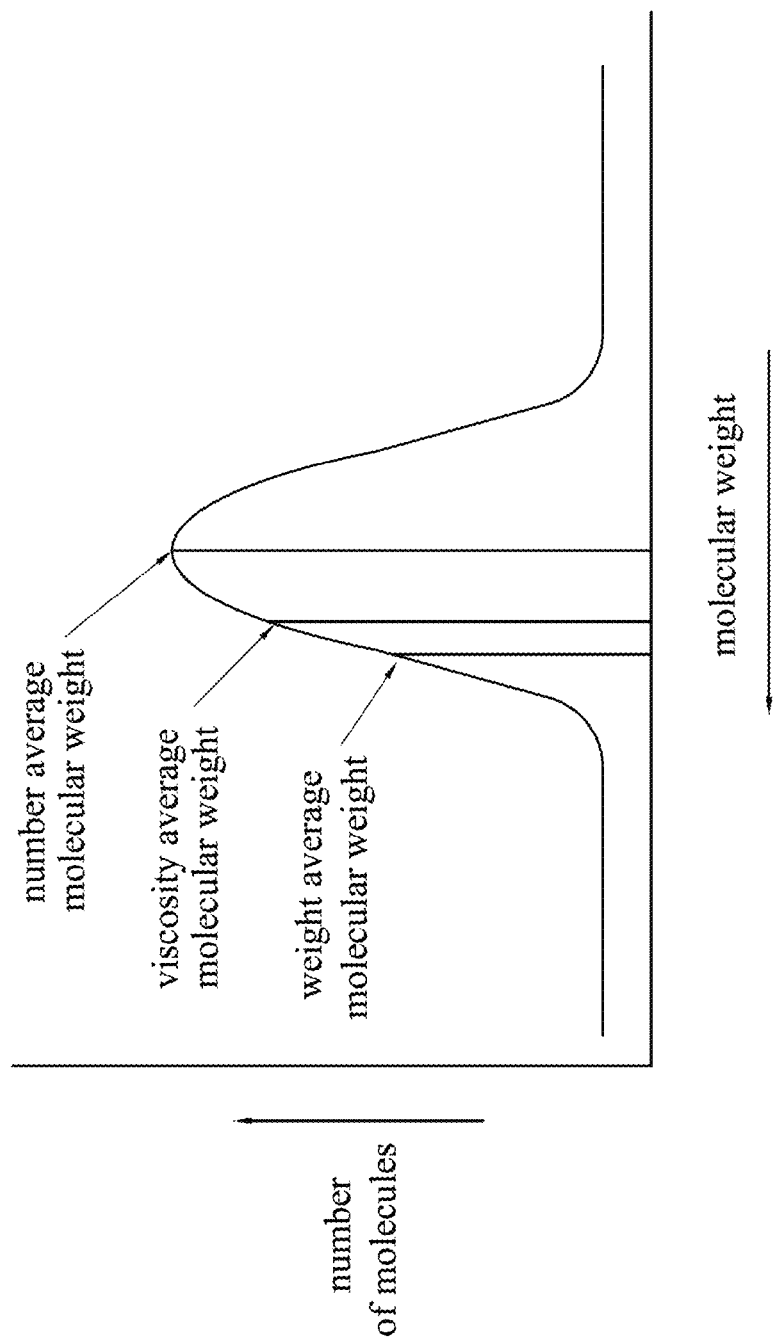
FIG. 2 is a distribution profile of polymer molecule weight related to numbers of polymer molecules.

Before further discussion, it should be mentioned that, commercially available CS and γ-PGA had molecules of various molecular weights, respectively, approximately ranging from 100K to 1,000K kDa, exhibiting Boltzmann distribution of different molecular weights, as shown in FIG. 2, which was also available at http://pslc.ws/macrog/weight.htm. It should be noted that, the molecular weight of FIG. 2 increased from right to left.

Moreover, as understood by a skilled person in the art, the commercially available CS and γ-PGA of different molecular weights also had different surface charges, respectively. The surface charges of various CS or γ-PGA of different molecular weights were obtained "only by measuring zeta potentials" rather than converting molecular weight.

6.1 The "zeta potential" of CS/γ-PGA claimed by the present invention MUST BE gotten or measured rather than being mathematically converted from its weight ratio.

Reference was made to Tables 3 and 4 according to Example 6, for clarifying that biodegradable carriers had the same "charge ratio" of CS/γ-PGA from different weight ratios of CS/γ-PGA, and not vice versa.

As shown in Table 3 of Example 6, 4 groups of the biodegradable carriers had the same "charge ratio" (for example, 4:1) of CS/γ-PGA, but they had different weight ratios due to different molecular weights of the CS and γ-PGA. According to the process of the present invention, the surface charge of the specific CS and γ-PGA was known "before mixing the carried substance, γ-PGA and CS", and all of the nanocomplexes having the same CS/γ-PGA charge ratio from different molecular weights of the CS and γ-PGA could be applied to deliver the carried substance.

TABLE 3

| | charge % (chitosan:r-pga) 4:1 | |
|---|---|---|
| | molecule weight (kDa) | wt % (chitosan:r-pga) |
| chitsan 1 (original) | 100-130K | 5.76:1 |
| chitsan 2 | 110K-150K | 4.72:1 |
| chitsan 3 | 60K-120K | 6.22:1 |
| chitsan 4 | 140K-220K | 5.85:1 |

PS. Chitsan 1 (original) refers to the one used in the present invention.

6.2 Biodegradable carriers having "the same weight ratios" of CS/γ-PGA contribute to different "charge ratio" of CS/γ-PGA.

As shown in Table 4 of the Supplement Example, the nanocomplexes have different charge ratios even they have the same CS/γ-PGA weight ratio (for example, 5.76:1) due to these nanocomplexes having different molecular weights of the CS and γ-PGA.

TABLE 4

| | 5.76:1 | |
|---|---|---|
| | molecule weight (kDa) | charge %(chitosan:r-pga) |
| chitsan 1 (original) | 100-130K | 4:1 |
| chitsan 2 | 110K-150K | 3.45:1 |
| chitsan 3 | 60K-120K | 5.12:1 |
| chitsan 4 | 140K-220K | 4.45:1 |

PS. Chitsan 1 (original) refers to the one used in the present invention.

6.3 The redundant experiments will be increased more if the zeta potentials of the carried substance, the first biodegradable macromolecule and the second biodegradable macromolecule DO NOT be measured.

In prior arts, it attempted to find out the best weight ratio of CS and γ-PGA from "dozens of weight ratios of CS and γ-PGA".

As aforementioned, CS and γ-PGA respectively included various molecules of different molecular weights, and one skilled in the art tried hardly to find out the best weight ratio of CS and γ-PGA from "dozens of weight ratios of CS and γ-PGA".

However, the prior art DID NOT measure the zeta potentials of the carried substance, the first biodegradable macromolecule and the second biodegradable macromolecule before mixing them, the resultant nanoparticles include positively and negatively charged ones in a preferable ratio must be obtained from "redundant" experiments.

6.4 The present invention makes the biodegradable carriers "only in a SINGLE test".

On the contrary with the prior art, according to the strategy of the present invention, the surface charges (i.e., zeta potentials) of the specific CS and γ-PGA are known, all of the nanocomplexes having the same CS/γ-PGA charge ratio from different molecular weights of the CS and γ-PGA could be applied to deliver the carried substance "only in single test", thereby successfully and substantially eliminating the testing numbers for finding out the best ratio of CS and γ-PGA, as shown in Table 1 of the present invention.

It should be supplemented that, the charged ratio of CS to γ-PGA in TABLE 1 of the present invention is merely as an example for delivering the DJ NS1 but is not limited thereto.

By the way, the immunogenic composition of the present invention could be applied in the field of vaccine compositions. Generally, the vaccine is preferably positively charged, so that it could improve the antigen presentation and enhance the T-cell-specific immune responses. The cationic surface charge of the CS/γ-PGA nanocomplex could enhance the antigen presentation efficiency as published on PNAS 112(2): 188-193, 2015. It was realized that the negatively charged biodegradable carriers are redundant in the vaccine composition.

Example 7

7.1 Development of DJ NS1-Encapsulated Nanocomplexes with Degradable Polymers by an Electro-Kinetic Approach.

The polymer-based nanocomplexes were produced using an electro-kinetic approach involving the ionic attraction of chitosan (positively-charged polymer) and γ-PGA (negatively-charged polymer), which are FDA-approved biodegradable polymers. DJ NS1 protein was introduced to form the nanocomplexes. The diameter of DJ NS1-encapsulated nanocomplexes was ~280 nm with a positive surface zeta potential, +13.8 mV, by quasi-elastic light scattering (QELS) measurement. Such nanocomplexes were stable for at least six months as shown in Table 5.

TABLE 5

The particle size and zeta potential of DJ NS1-encapsulated nanocomplexes.

| | DJ NS1 | DJ NS1-encapsulated nanocomplexes | empty nanocomplexes | AuNP[b] |
|---|---|---|---|---|
| Particle size[a] (nm) | 7.4 ± 0.8 | 284.0 ± 30.8 | 268.0 ± 55.2 | 15.9 ± 0.6 |
| Zeta potential[a] (MV) | −30.2 ± 1.3 | 13.8 ± 0.5 | 30.5 ± 2.2 | −38.6 ± 2.3 |

[a]The particle size and zeta potential of 10-fold diluted nanocomplexes were measured by quasi-elastic light scattering (QELS) analyzer (632 nm He—Ne laser, 10,000:1 polarity, 5 mW) at 25° C. (n = 3)
[b]The 13-nm gold nanoparticle solution (AuNP, 10 nM) served as a measurement reference control.

Figure 3A:
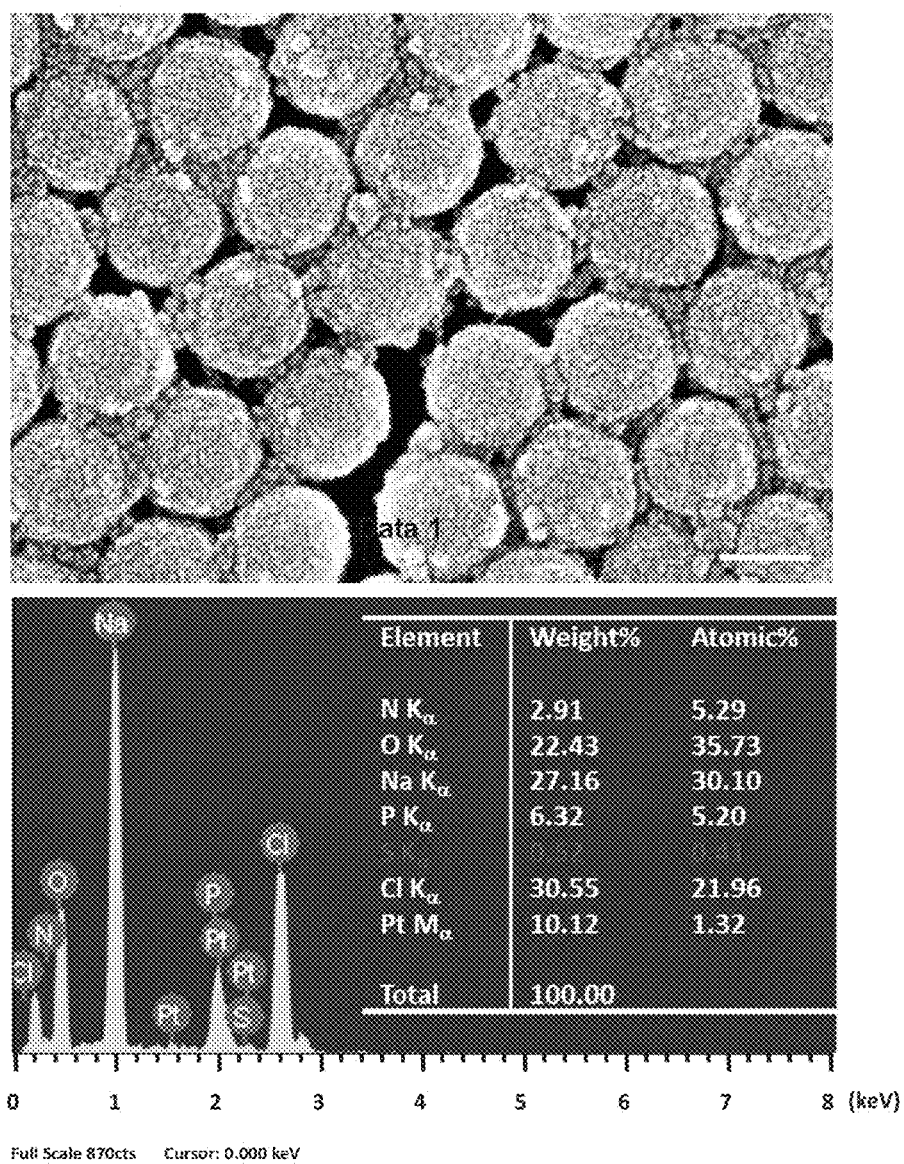
FIGS. 3a to 3c show morphological images and composition analysis profile of DJ NS1-encapsulated nanocomplexes according to an embodiment of the present invention.

Compared with empty nanocomplexes, encapsulated nanocomplexes possessed larger particle size and lower positive surface charge, likely resulting from negatively-charged DJ NS1 (Table 5). Field-emission scanning electron microscopy (FE-SEM) analysis showed the particle size was about 250 nm, as shown in FIG. 3a. As expected, the measured size was slightly smaller than that determined by quasielastic light scattering (QELS) analysis, since the former measures the "solid" particle diameter without the hydrodynamic layer as shown in FIGS. 3d and 3e. FIG. 3d was a profile of the stability of the immunostimulatory nanocomplexes measured by quasi-elastic light scattering (QELS) spectrometer (632 nm He—Ne laser, 10,000:1 polarity, 5 mW). FIG. 3e was an electrophoretic phase plot of the immunostimulatory nanocomplexes monitored by photon correlation spectrometer (PCL).

Figure 3B:
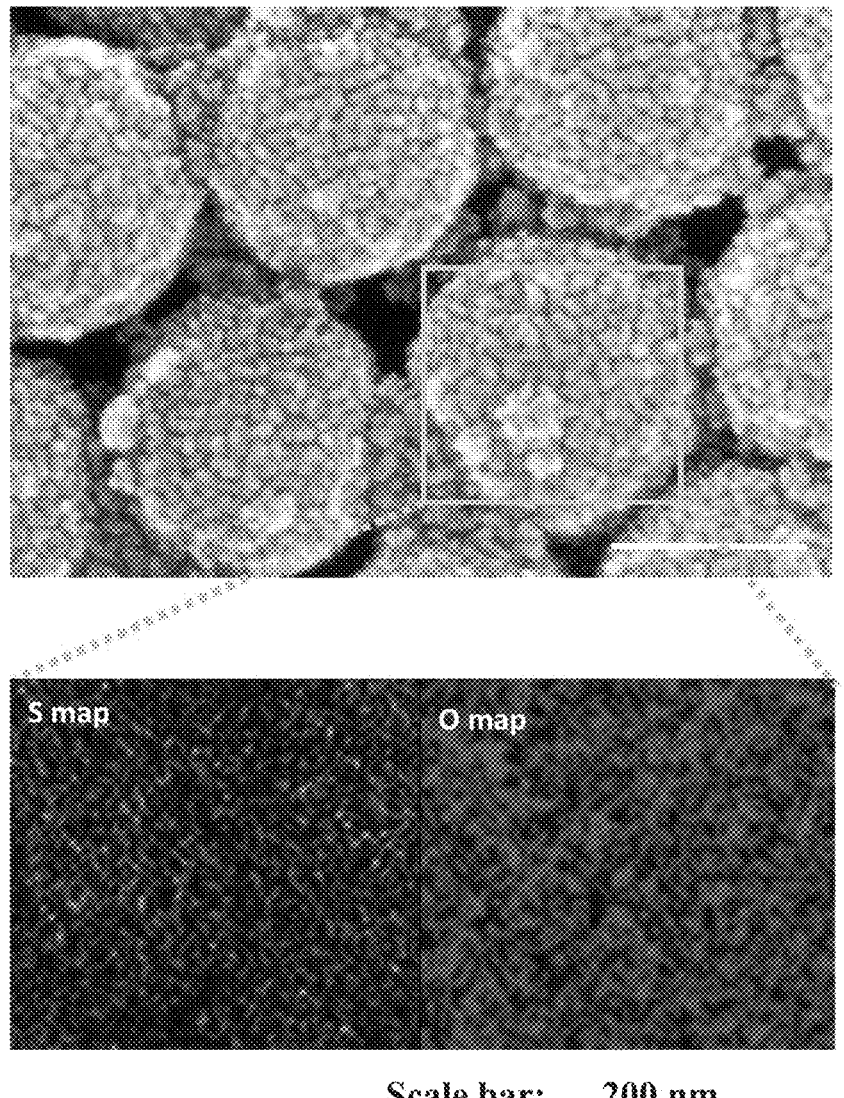
Figure 3C:
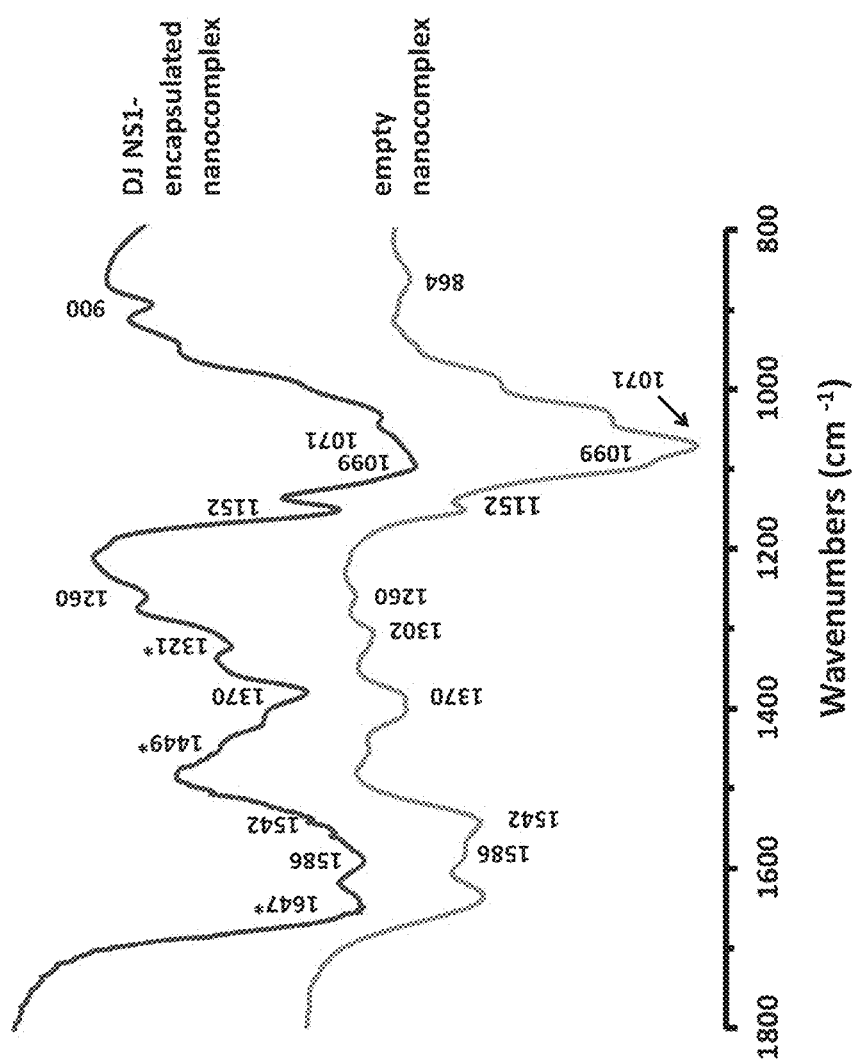
Figure 3D:
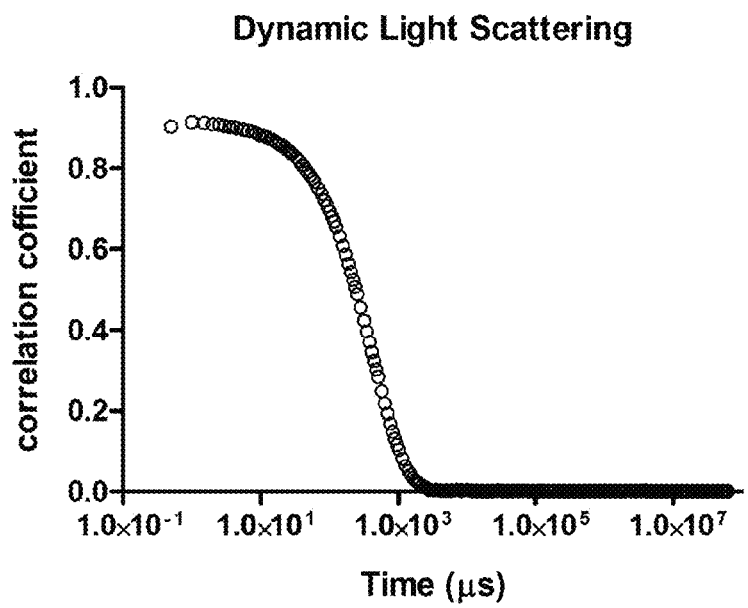
FIG. 3d is a profile of the stability of the immunostimulatory nanocomplexes measured by quasi-elastic light scattering (QELS) spectrometer (632 nm He—Ne laser, 10,000:1 polarity, 5 mW).
Figure 3E:
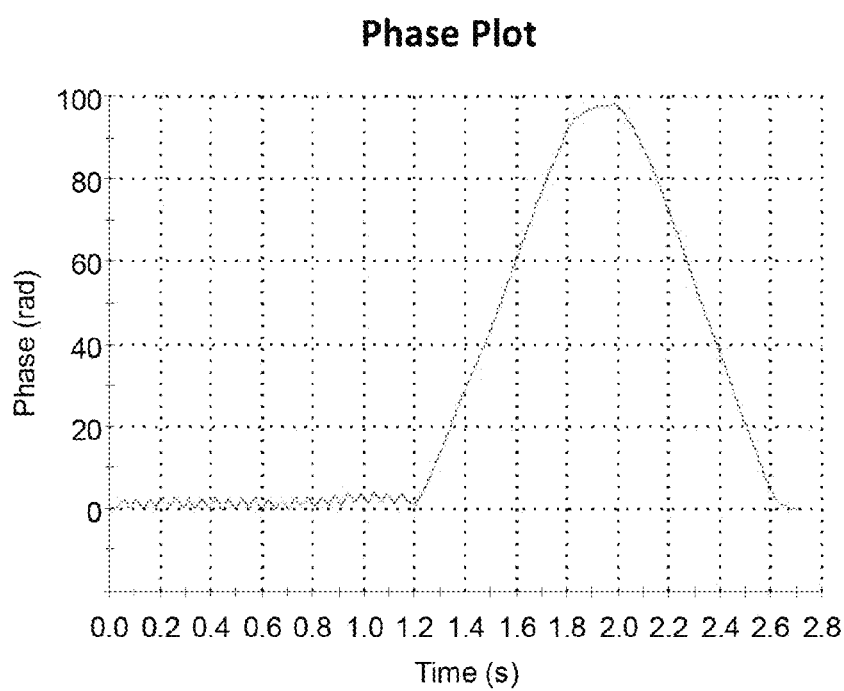
FIG. 3e is an electrophoretic phase plot of the immunostimulatory nanocomplexes monitored by photon correlation spectrometer (PCL).

Energy-dispersive X-ray spectroscopy (EDX) demonstrated the existence of DJ NS1 protein (detected by sulfur content) in nanocomplexes (FIG. 3b). The composition of DJ NS1-encapsulated nanocomplexes was further analyzed by Fourier transformed infrared spectroscopy (FT-IR), as shown in FIG. 3c. Wavenumber assignments were 864 cm$^{-1}$ (—C—O—C skeletal mode), 900 cm$^{-1}$ (β-glucose, —C—O—C skeletal mode), 1071 cm$^{-1}$ (glucose), 1099 and 1152 cm$^{-1}$ (C—N vibration mode), 1260 cm$^{-1}$ (amide ill, unordered), 1302 cm$^{-1}$ (amide III), 1321 cm$^{-1}$ (amide III, α helix), 1370 cm$^{-1}$ (saccharide band), 1449 cm$^{-1}$ (C—H bending in protein), 1542 cm$^{-1}$ (—NH$^{3+}$ vibration mode of chitosan), 1586 cm$^{-1}$ (—COO$^{-}$ vibration mode of γ-PGA), and 1647 cm$^{-1}$ (amide I, α helix). Signals at 1321, 1449 and 1647 cm$^{-1}$ derived from the characteristic vibration modes of protein structures. Those results were clear evidence for the encapsulation of DJ NS1 protein with a homogeneous distribution into nanocomplexes. The loading content and loading efficiency of DJ NS1 protein in nanocomplexes were 72% and 27%, respectively, as determined by high-performance liquid chromatography (HPLC).

7.2 Active Immunization with DJ NS1 Protein Encapsulated in Nanocomplexes Induces Higher Levels of DJ NS1-Specific Abs than DJ NS1 Combined with Alum.

To investigate the Ab responses induced by DJ NS1-encapsulated nanocomplexes, C3H/HeN mice were subcutaneously immunized with 25 μg/mouse of DJ NS1 protein in nanocomplexes or alum. Alum had been widely used as a standard adjuvant for human vaccines. After two rounds of immunization, the DJ NS1-specific Ab titers were determined in the mouse sera.

The mice inoculated with DJ NS1-encapsulated nanocomplexes elicited titers of $2^7$ (×10$^3$) for anti-DJ NS1 IgG and $2^4$ (×10$^3$) for anti-DJ NS1 IgM, whereas the mice inoculated with DJ NS1 plus alum elicited titers of only $2^4$ (×10$^3$) for anti-DJ NS1 IgG and $2^3$ (×10$^3$) for anti-DJ NS1 IgM. Based on these results, DJ NS1-encapsulated nanocomplexes could induce higher specific IgG and IgM titers when compared with DJ NS1 plus alum.

The safety of DJ NS1-encapsulated nanocomplexes was evaluated by examining the cytotoxicity both in vitro and in vivo. After incubation of THP-1 cells with serial dilutions of DJ NS1-encapsulated nanocomplexes or nanocomplexes alone for 24, 48 or 72 h, the cells were assayed for the release of lactate dehydrogenase (LDH), as shown in FIGS. 4a to 4c.

Figure 4A:
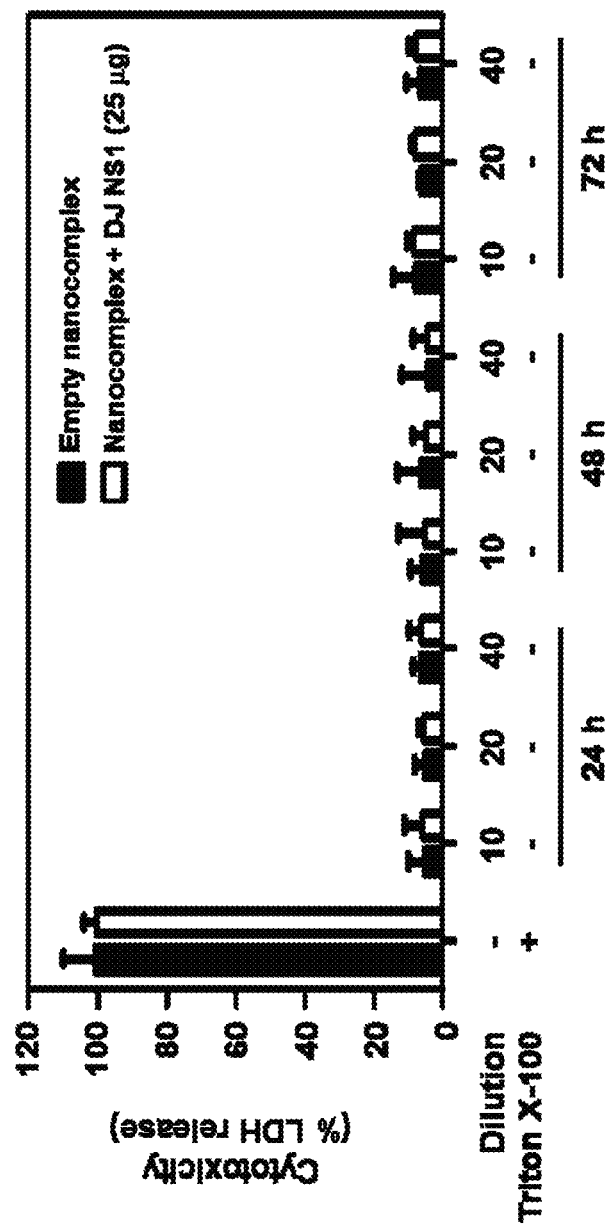
Figure 4B:
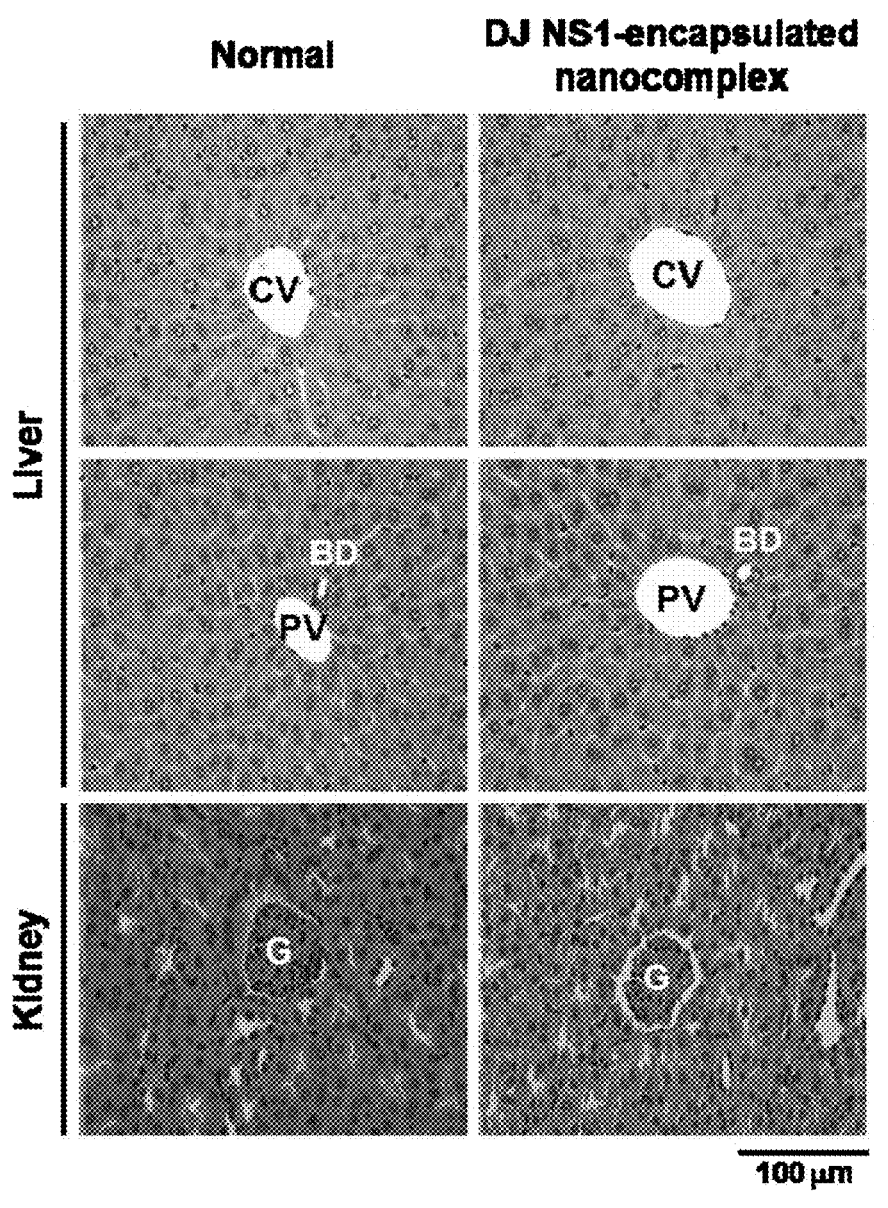
Figure 4C:
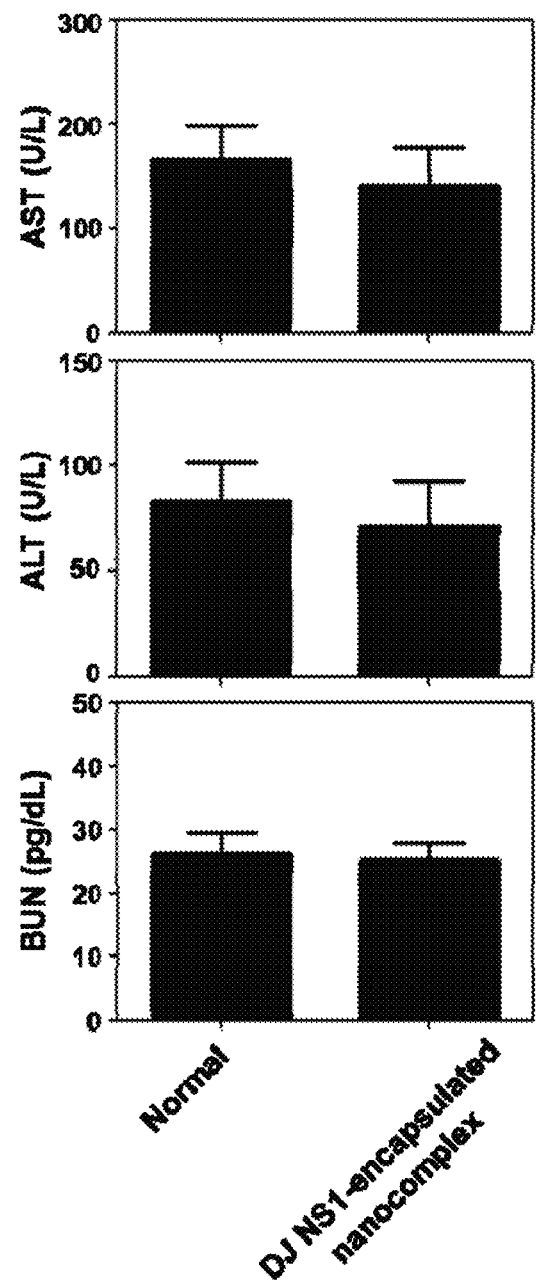

There was no significant change in LDH release when cells were treated with DJ NS1-encapsulated nanocomplexes or nanocomplexes alone in serial dilutions, as shown in FIG. 4a. Histological examination of the liver and kidney tissues from mice immunized with DJ NS1-encapsulated nanocomplexes showed no significant difference as compared to the normal control group, as shown in FIG. 4b. In addition, there were no significant changes in the serum levels of AST, ALT and BUN between these two groups, as shown in FIG. 4c. The bleeding time was determined at 3 days post-infection. P<0.01, *P<0.001, NS: not significant; one-way ANOVA with Tukey's post-test.

Figure 5A:
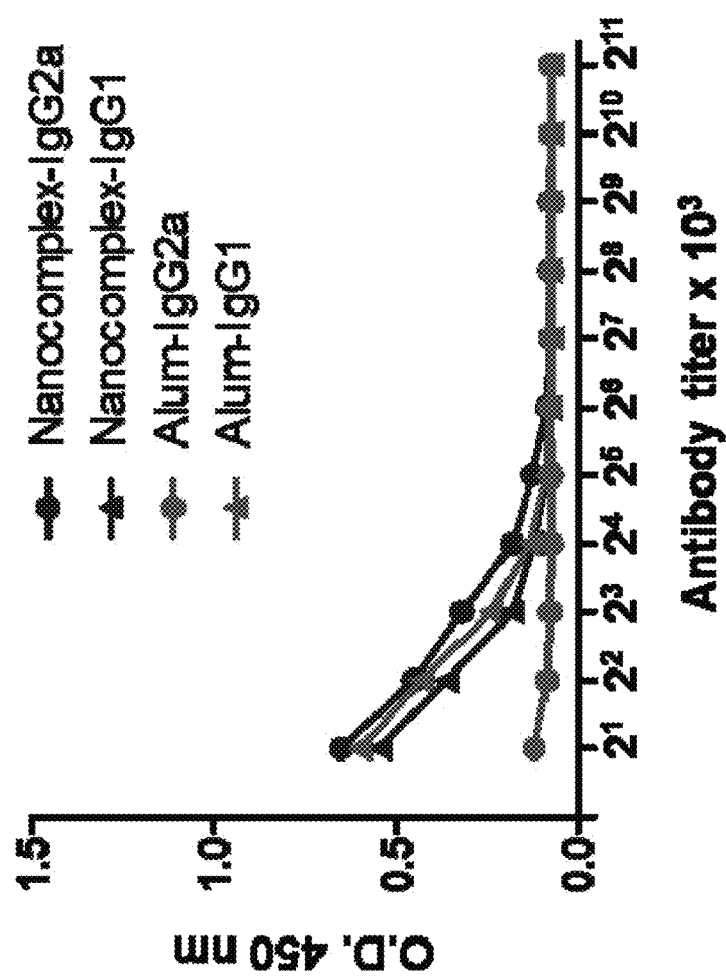
FIGS. 5a to 5c show antibody titers (FIGS. 5a and 5b) and cytokine profiles (FIG. 5c) of mice immunized with DJ NS1-encapsulated nanocomplexes or nanocomplexes alone according to an embodiment of the present invention.
Figure 5B:
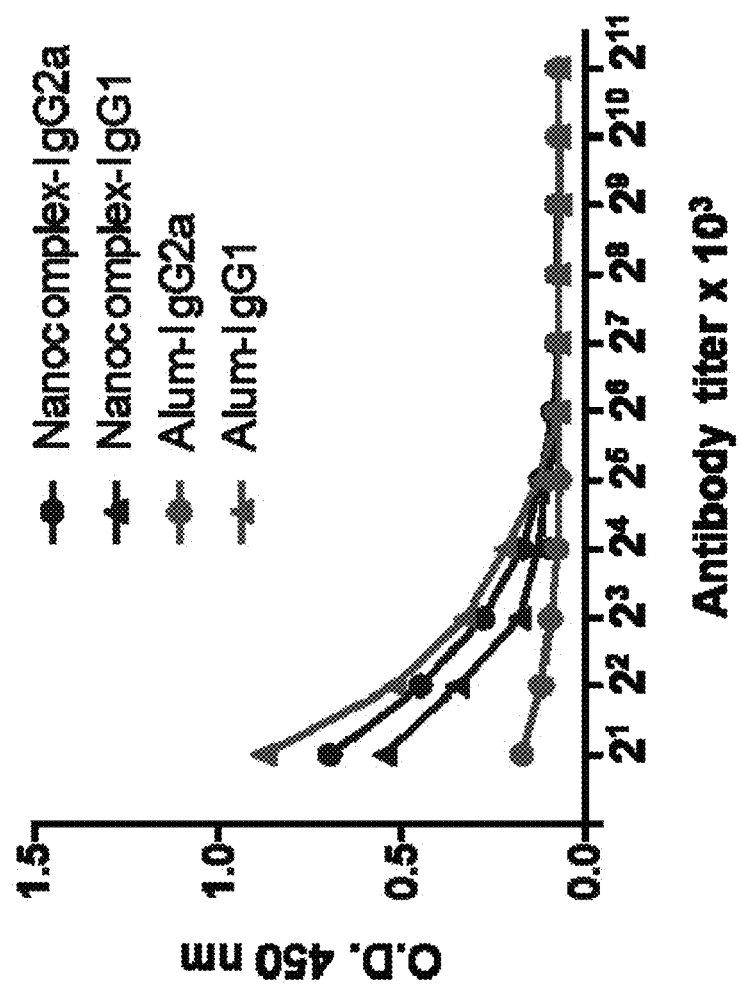
Figure 5C:
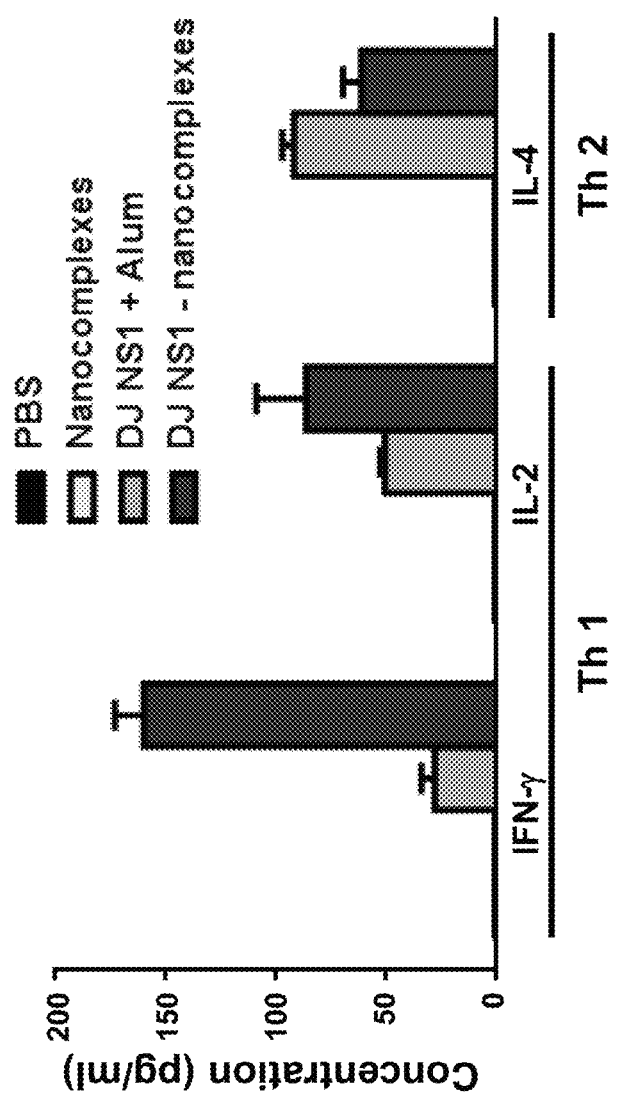
Figure 6A:
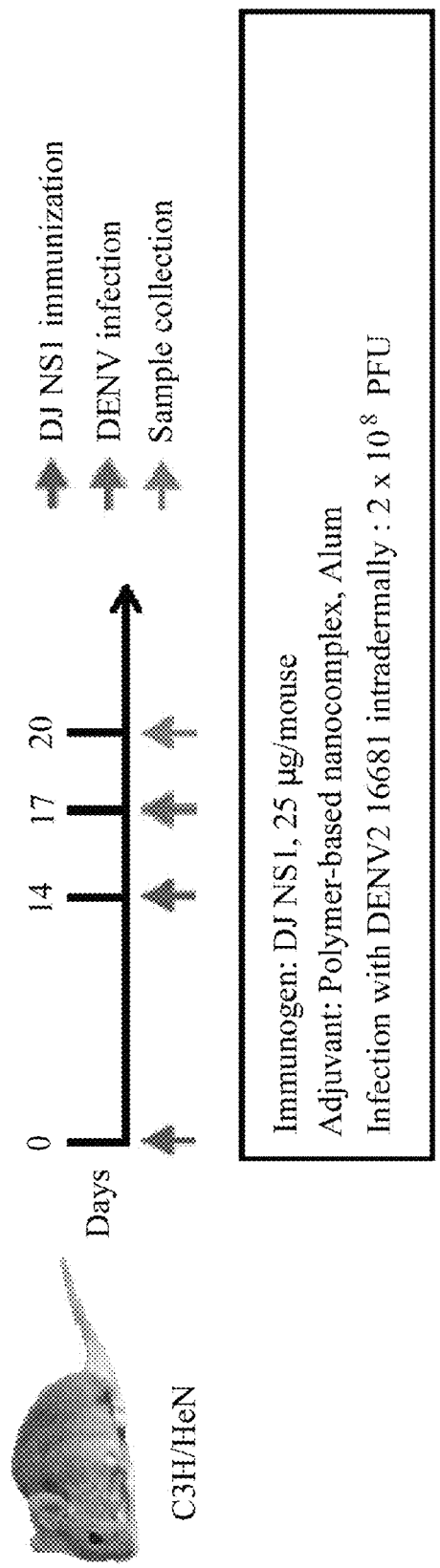
FIGS. 6a to 6b show active immunization results with DJ NS1-encapsulated nanocomplexes decreases DENV-induced prolonged bleeding time according to an embodiment of the present invention.
Figure 6B:
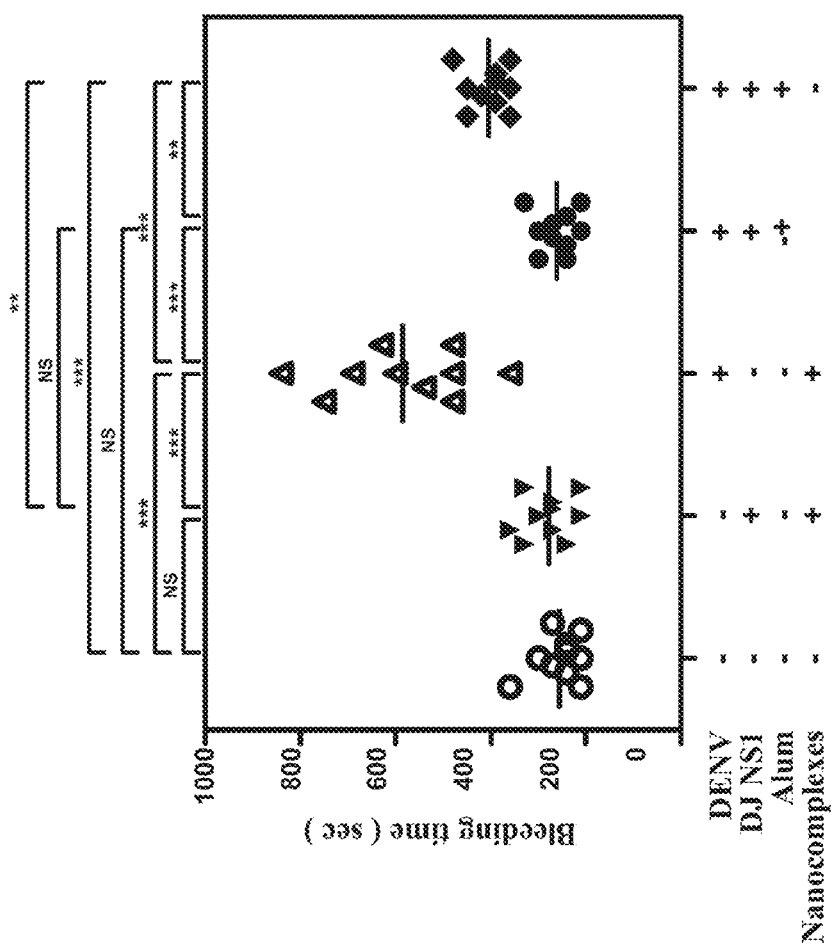
Figure 7B:
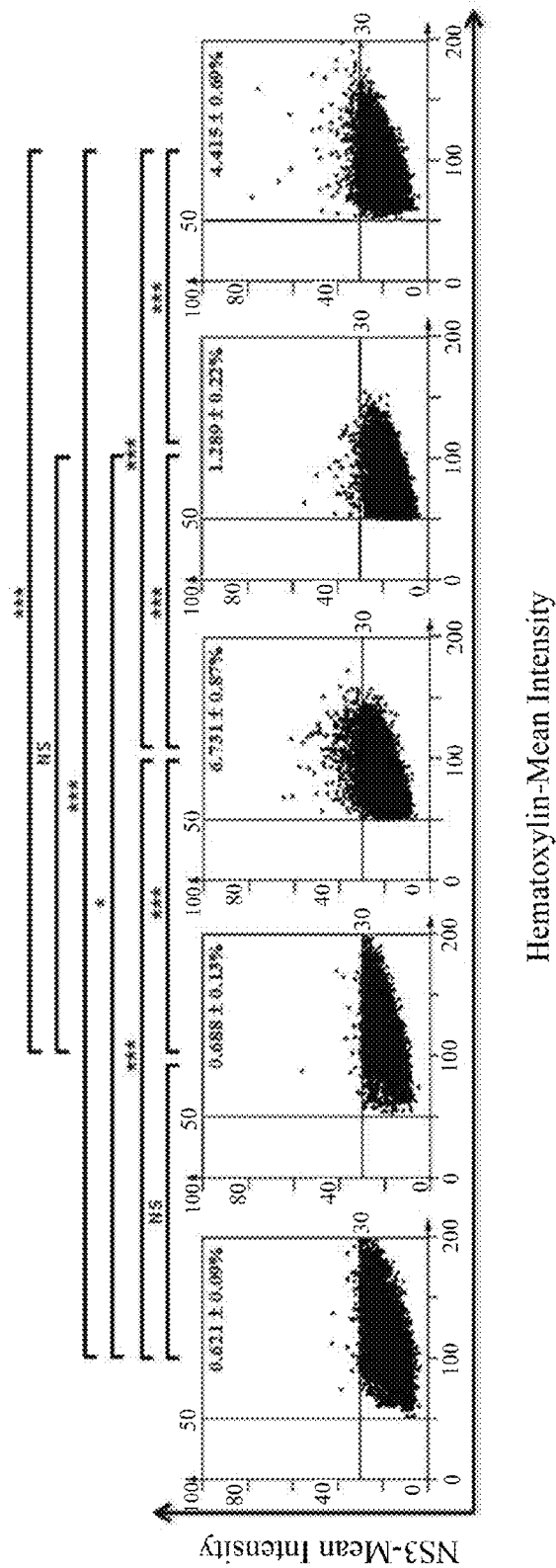
Figure 8A:
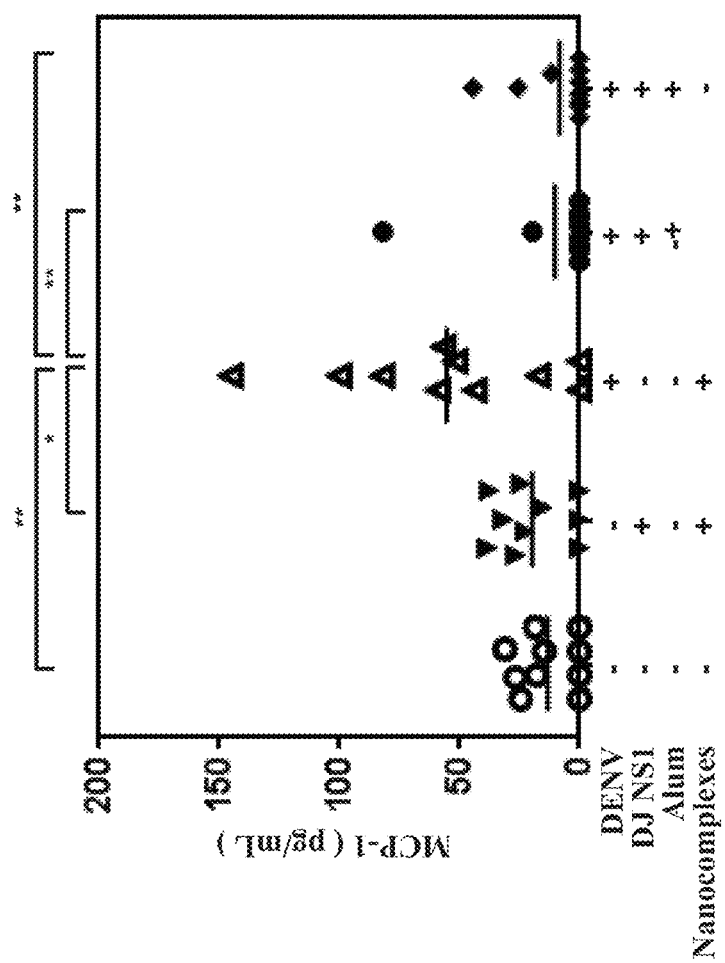
FIGS. 8a to 8c show active immunization results with DJ NS1-encapsulated nanocomplexes reduces macrophage infiltration at the skin inoculation site according to an embodiment of the present invention. The mice were intradermally inoculated with medium (Mock) or DENV2 16681
Figure 8B:
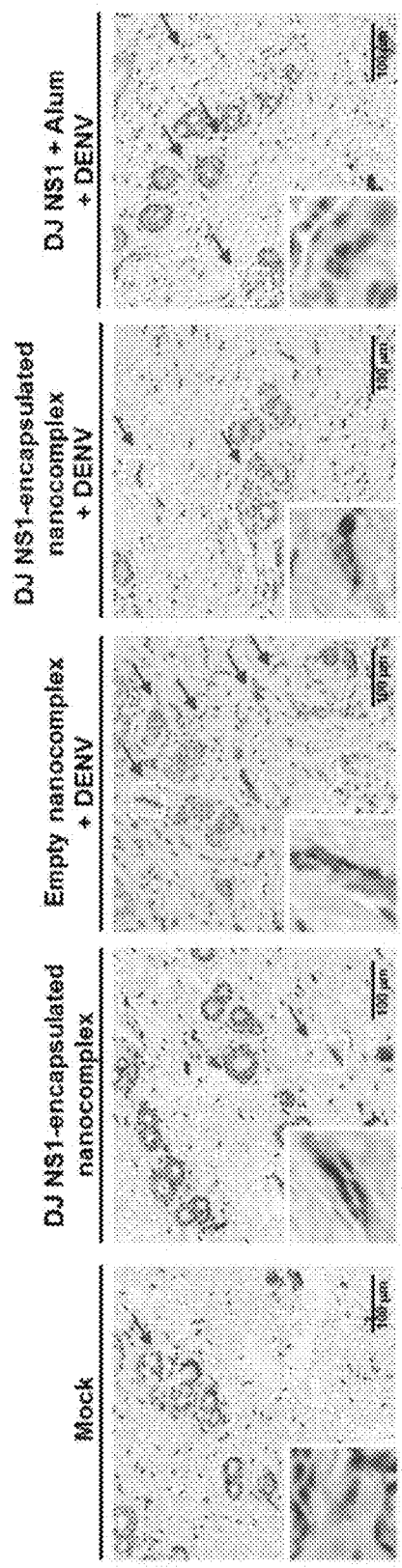
Figure 8C:
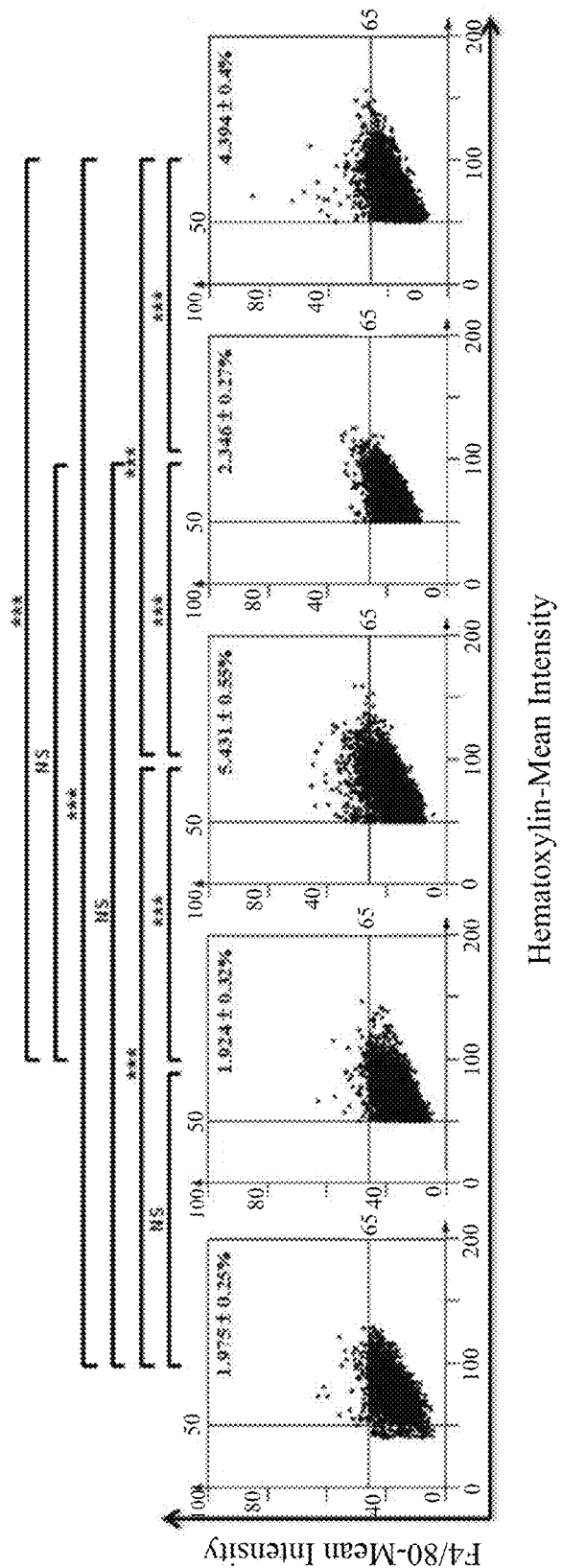
Figure 9A:
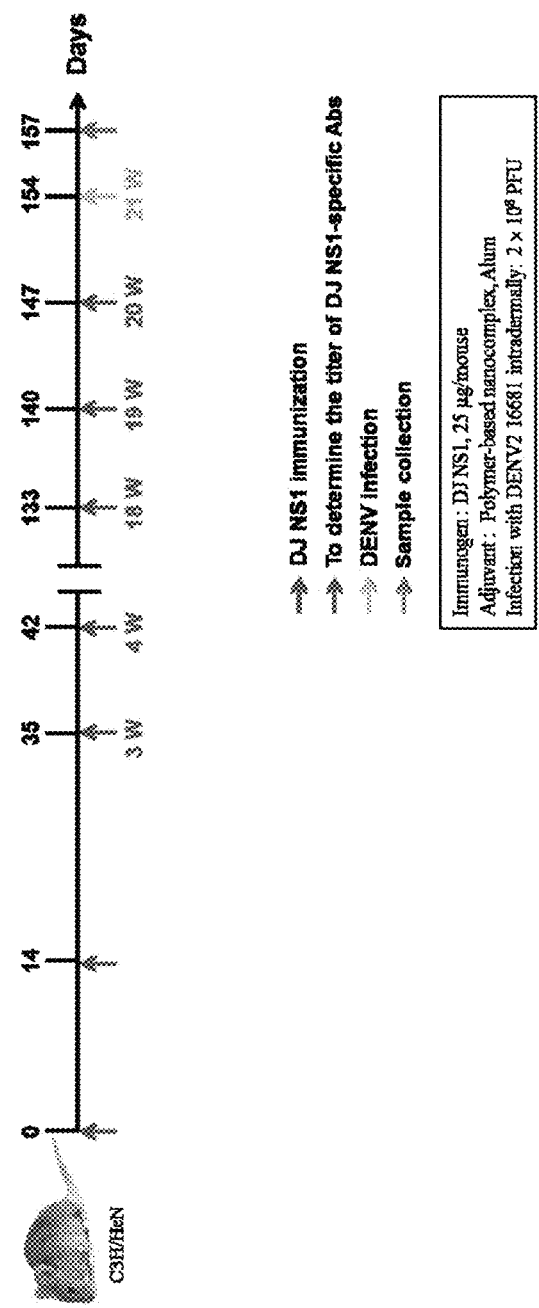
Figure 9B:
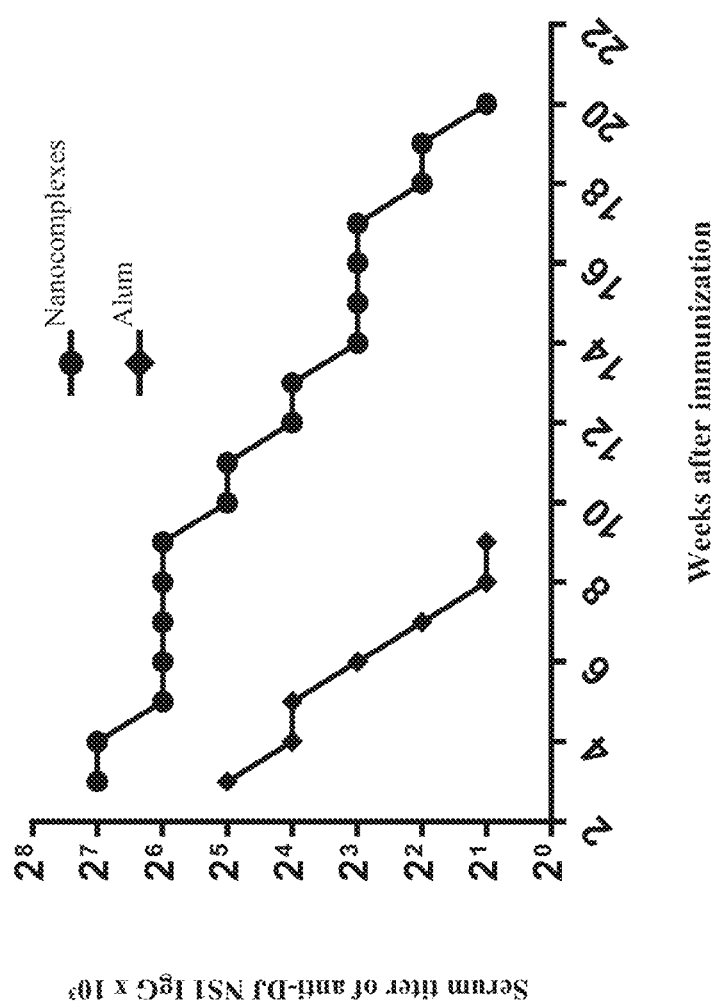
Figure 9D:
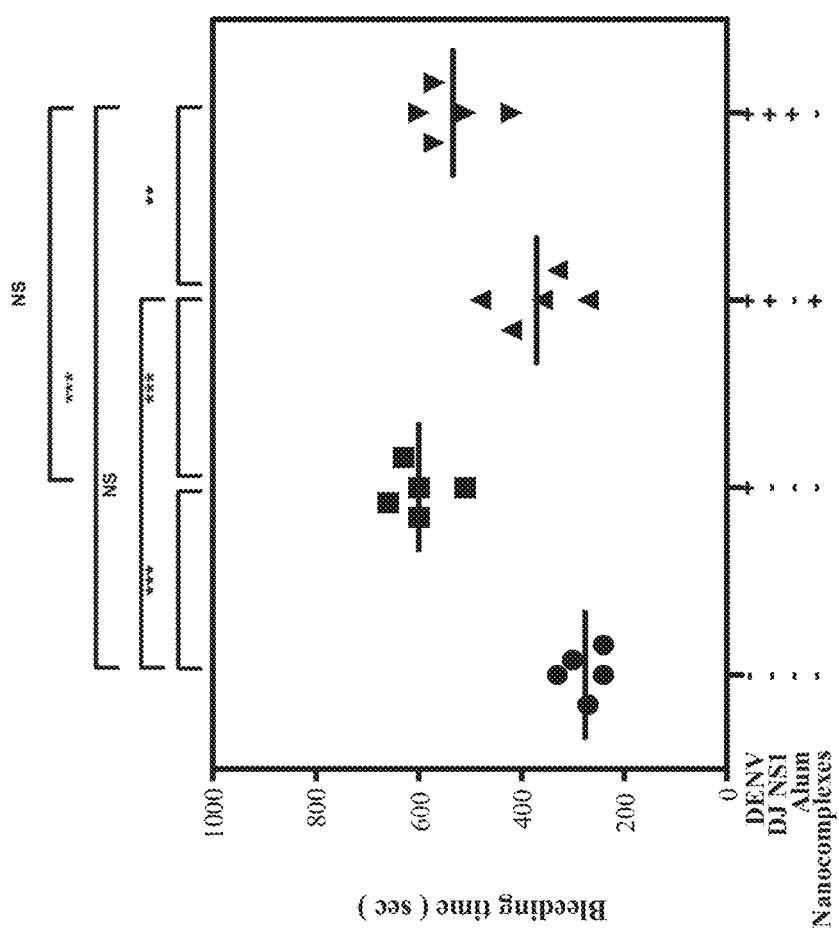
Figure 10B:
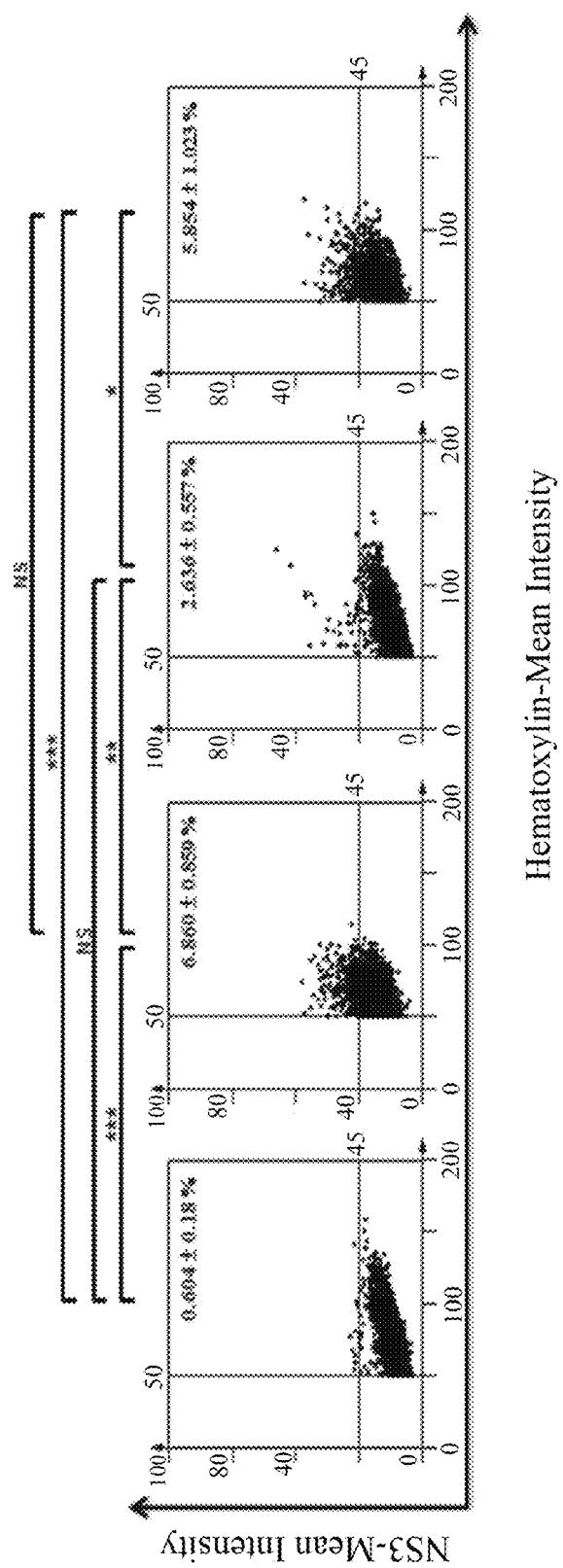
Figure 10C:
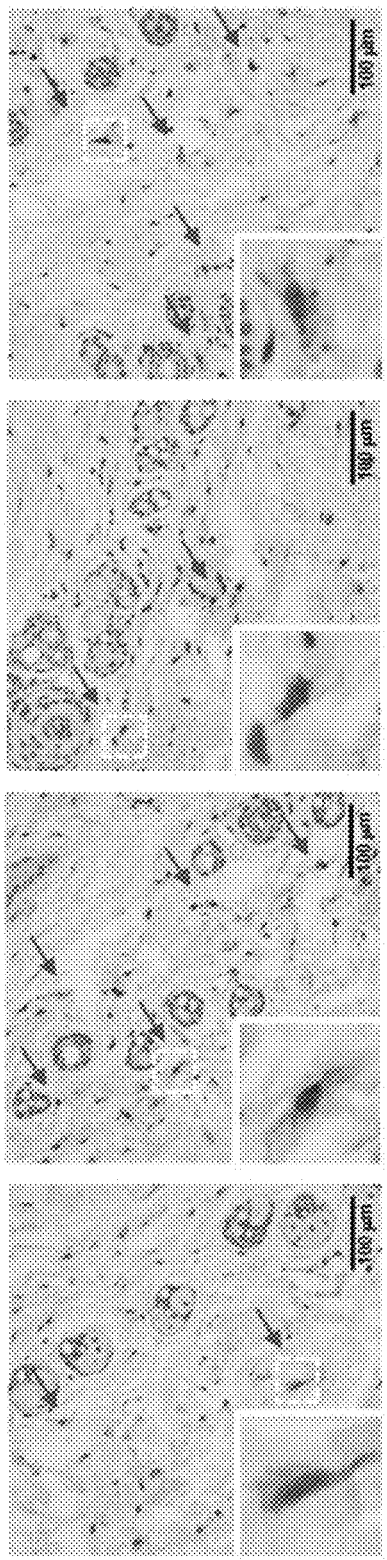
Figure 10D:
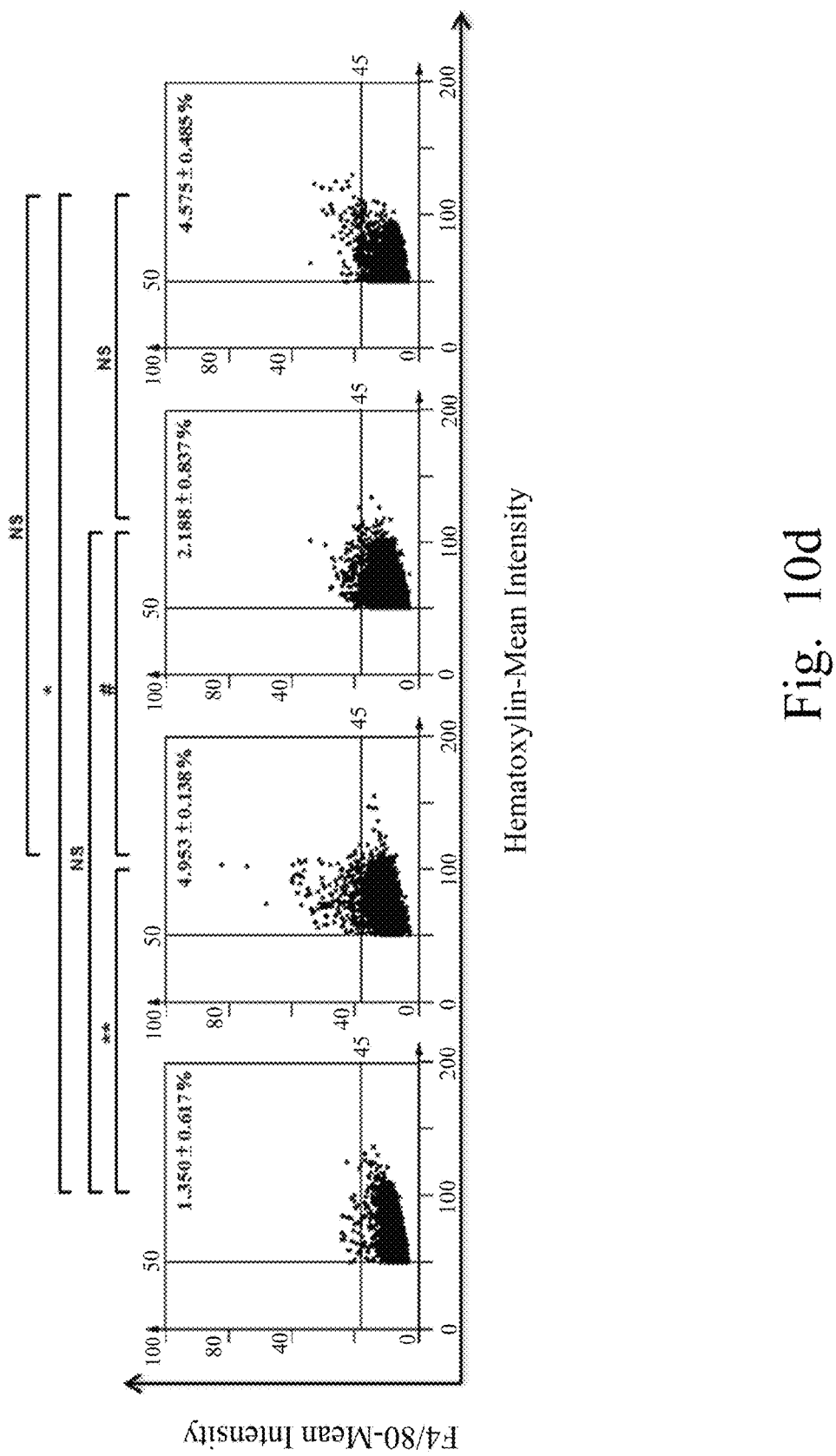

Alum adjuvant could provoke a strong Th2 response, whereas certain particulates such as various vesicles may induce a Th1 or Th2 response depending on their size. Therefore, the levels of DJ NS1-specific IgG2a and IgG1 Abs for Th1 and Th2 responses were determined, respectively, in mouse sera after two rounds of immunization. The results showed that DJ NS1-encapsulated nanocomplexes can induce both IgG1 and IgG2a Abs, while DJ NS1 plus alum mainly induced IgG1 Abs, as shown in FIGS. 5a and 5b. To determine the cytokine profiles, lymphocytes were collected from immunized mice and re-stimulated with 5 μg/ml of DJ NS1 for 72 h. Cytokine concentrations including IFN-γ, IL-2 and IL-4 in the culture supernatants were determined. The cytokine profiles showed higher Th1 cytokine levels (i.e., IFN-g and IL-2) in the NS1-encapsulated nanocomplexes-treated group as compared with the NS1 plus alum-treated group. Both DJ NS1-encapsulated nanocomplexes and DJ NS1 plus alum induced the Th2 cytokine, IL-4, although DJ NS1 plus alum induced higher levels than did DJ NS1-encapsulated nanocomplexes, as shown in FIG. 5c. These results indicated that DJ NS1-encapsulated nanocomplexes induce both Th1 and Th2 responses, while DJ NS1-adsorbed alum mainly induces a Th2 response.

7.3 Active Immunization with DJ NS1-Encapsulated Nanocomplexes Decreases DENV-Induced Prolonged Bleeding Time, and Reduces Viral NS3 Antigen Expression and Macrophage Infiltration at the Skin Inoculation Site.

Our previous study showed that anti-DJ NS1 Abs provided protective effects against DENV infection in mice. In this study, the protective effects of DJ NS1 protein were further evaluated by using nanocomplexes as adjuvant. Following immunization of mice with 25 μg/mouse of DJ NS1 protein in nanocomplexes or alum, mice were challenged with $2\times10^8$ PFU/mouse of DENV and the tail bleeding time was determined at 3 days post-infection, as shown in FIG. 6*a*. Results showed that the prolonged bleeding time induced by DENV was significantly reduced in the DJ NS1-encapsulated nanocomplexes group than in the DJ NS1-adsorbed alum group. Moreover, the bleeding time of mice immunized with DJ NS1-encapsulated nanocomplexes, followed by DENV challenge, was similar to that of non-infected mice, as shown in FIG. 6*b*.

The dengue antigen expression was determined at the local injection site at 3 days post-infection by immunohistochemical staining for dengue NS3 protein as a marker for viral replication. The stained images were further quantified by HistoQuest software. The results of HistoQuest analysis showed that the percentage of NS3-positive cells was significantly decreased in the DJ NS1-encapsulated nanocomplexes group as compared with the groups given either nanocomplexes alone or DJ NS1 plus alum, as shown in FIGS. 7*a* and 7*b*.

MCP-1 is a highly expressed chemokine in DHF/DSS patients and can be presented on the surface of high endothelial venules for recruitment of monocytes. In the mouse model, MCP-1 contributes to attracting macrophages in response to DENV infection. Following, the levels of MCP-1 in mouse serum and the levels of F4/80-positive macrophages infiltrated to the dermis layer were determined. Results showed that active immunization with DJ NS1-encapsulated nanocomplexes reduced DENV-induced MCP-1 production, as shown in FIG. 8*a*. The results of immunohistochemical staining and HistoQuest analysis showed that the percentage of F4/80-positive macrophages was significantly reduced in the DJ NS1-encapsulated nanocomplexes group as compared with the groups given either nanocomplexes alone or DJ NS1 plus alum, as shown in FIGS. 8*b* and 8*c*.

7.4 Active Immunization with DJ NS1-Encapsulated Nanocomplexes can Provide Long-Lasting Ab Responses and Long-Term Protection.

A successful dengue vaccine must achieve several criteria, one of which is to provide long-lasting immunity. In this EXAMPLE, the Ab responses in mice inoculated were compared with 25 μg of DJ NS1 protein combined with either nanocomplexes or alum. After two arounds of immunization, the DJ NS1-specific IgG and IgM titers were determined in mouse sera every week, as shown in FIG. 9*a*. Results showed that the Ab titers induced by DJ NS1-encapsulated nanocomplexes remained detectable till 18-19 weeks after immunization. In contrast, the Ab titers induced by DJ NS1 plus alum could be detected only up to 8 weeks after immunization, as shown in FIGS. 9*b* and 9*c*.

To determine whether active immunization with DJ NS1-encapsulated nanocomplexes can protect against the DENV-induced prolonged bleeding time, mice were challenged with $2\times10^8$ PFU/mouse of DENV at 21 weeks after immunization, and then determined the bleeding time at 3 days post-infection. The results showed that active immunization with DJ NS1-encapsulated nanocomplexes significantly reduced the DENV-induced prolonged bleeding time when compared with the DJ NS1 plus alum group, as shown in FIG. 9*d*. The mouse sera was also collected on 3 days post-infection to determine the DJ NS1-specific Ab titers after DENV infection.

Results showed that mice inoculated with DJ NS1-encapsulated nanocomplexes induced an anti-DJ NS1 IgG titer of $2^6$ ($\times10^3$). In contrast, mice inoculated with DJ NS1 plus alum showed an anti-DJ NS1 IgG titer of only $2^4$ ($\times10^3$). These results indicate that mice immunized with DJ NS1-encapsulated nanocomplexes induce higher Ab responses than mice immunized with DJ NS1 plus alum.

The level of DENV antigen NS3 expression was determined at the local infection site, by immunohistochemical staining at 3 days post-infection. The stained images were quantified by HistoQuest software. The results of HistoQuest analysis showed that the percentage of NS3-positive cells was significantly decreased in the DJ NS1-encapsulated nanocomplexes group as compared with the DENV alone or DJ NS1 plus alum groups, as shown in FIGS. 10*a* and 10*b*.

The level of F4/80-positive macrophage infiltration was also determined in the skin inoculation site at 3 days post-infection by immunohistochemical staining. After quantification by HistoQuest software, the results showed that the percentage of F4/80-positive macrophages was significantly reduced in the DJ NS1-encapsulated nanocomplexes group as compared with the DENV alone or DJ NS1 plus alum groups, as shown in FIGS. 10*c* and 10*d*.

Example 8: Evaluation of Nanocomplex with Different Charge Distribution

A low-MW CS was obtained from the depolymerization of a commercially available CS. Given a low-MW, the polycationic CS had a good solubility at a pH value close to physiological range. CS (MW 280 kDa) with a degree of deacetylation of approximately 85% (Sigma-Aldrich, St. Louis, Mo., USA) was treated with sodium perborate tetrahydrate (NaBO3, Sigma-Aldrich) to produce low-MW CS.

Sample 1

First, the zeta potential of sample of 25 μg of DJ-NS1 protein in 1 ml and aqueous γ-PGA (1 mg/ml, 1 ml, i.e. polymer 1), was measured, respectively. The difference of zeta potential (polymer/minus carried substance) was about 10 mV. And these two solutions were premixed, followed by adding into aqueous CS (3 mg/ml, 3 ml, i.e. polymer 2) under magnetic stirring in the 10 mM phosphate buffer (pH=6) at 25° C., for forming the nanocomplex of Sample 1 (final zeta potential: 11.7±0.6 mV, particle size: 278.0±22.5 nm).

Sample 2

First, the zeta potential of sample of 25 μg of DJ-NS1 protein in 1 ml and aqueous γ-PGA (1 mg/ml, 1 ml, i.e. polymer 1), was measured, respectively. The difference of zeta potential (polymer/minus carried substance) is about 10 mV. Next, added the polymer 2 (CS, 3 mg/ml, 10 ul) into the polymer 1 solution, and now the difference of zeta potential (polymer/minus carried substance) is about 16 mV. These two solutions were premixed, followed by adding into aqueous CS (3 mg/ml, 3 ml, i.e. polymer 2) under magnetic stirring in the 10 mM phosphate buffer (pH=6) at 25° C., for forming the nanocomplex of Sample 2 (final zeta potential: 11.6±0.5 mV, particle size: 270.0±23.2 nm).

Sample 3

First, the zeta potential of sample of 25 μg of DJ-NS1 protein in 1 ml and aqueous γ-PGA (1 mg/ml, 1 ml, i.e.

polymer 1), was measured, respectively. The difference of zeta potential (polymer/minus carried substance) is about 10 mV. Next, added the polymer 1 (γ-PGA, 1 mg/ml, 10 ul) into the polymer 1 solution, and now the difference of zeta potential (polymer/minus carried substance) is about 3 mV. These two solutions were premixed, followed by adding into aqueous CS (3 mg/ml, 3 ml, i.e. polymer 2) under magnetic stirring in the 10 mM phosphate buffer (pH=6) at 25° C., for forming the nanocomplex of Sample 3 (final zeta potential: 11.6±0.6 mV, particle size: 281.0±20.2 nm).

Figure 11:
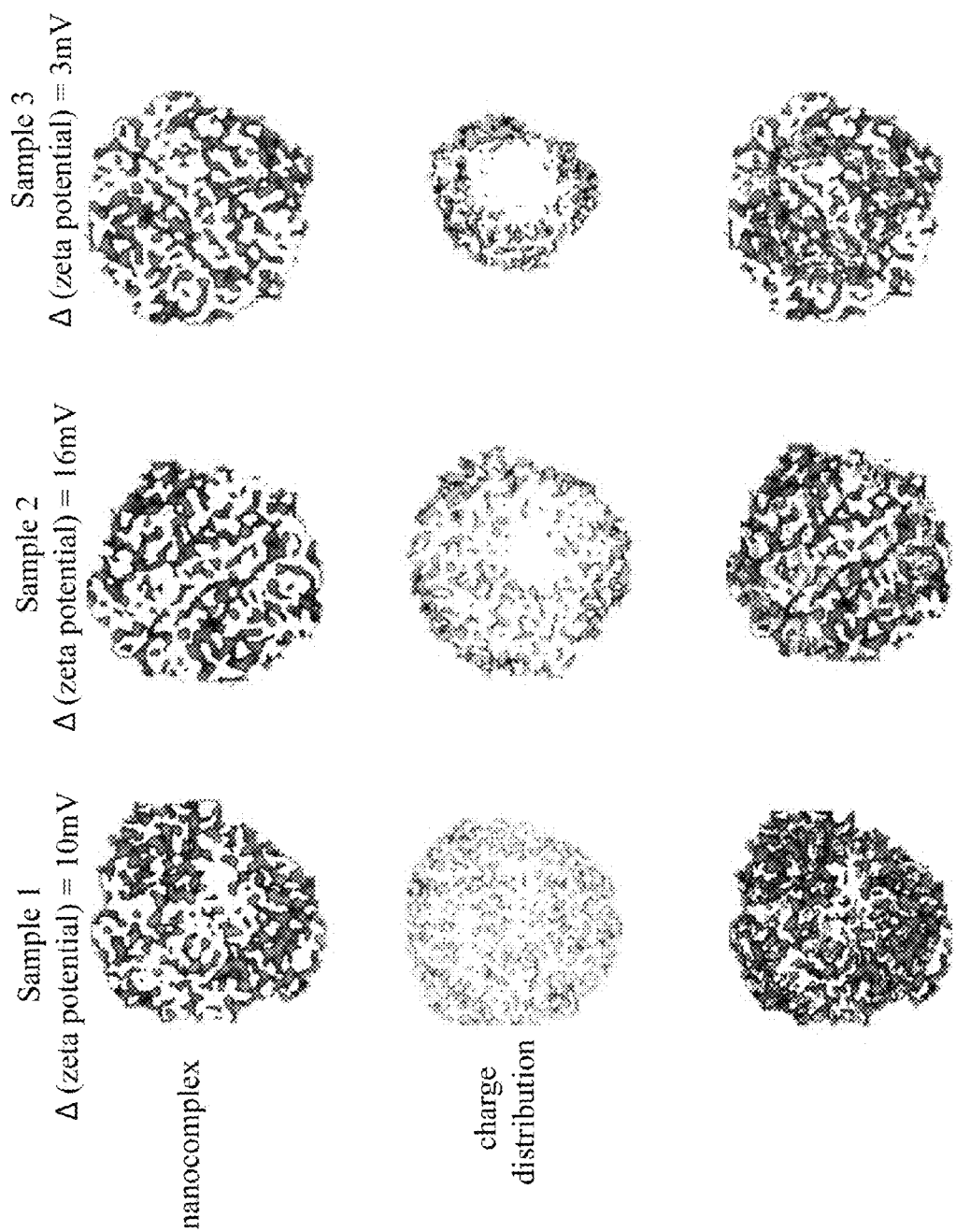
FIG. 11 shows images of molecular distributions (the images at the top row), the positively charge distributions (the images at the middle row) and the combined distributions (the images at the bottom row) of the nanocomplexes of Samples 1 to 3 of Example 8 according to some embodiments of the present invention.

Reference was made to FIG. 11 according to Samples 1 to 3 of Example 8. Nonuniformly (or spatially inhomogeneous) charge distribution could be imaged by the STM (Scanning Tunneling Microscopy) via the point-by-point collection of a large number of individual charge collection efficiency values. Charge distribution images of FIG. 11 were produced by recording an electric current during a two-dimensional scan of the fabricated nanocomplex. The experiments were performed with a home-made low temperature STM, which is capable of cooling the STM and the sample down to 20 K. The STM and sample preparation station are housed in a ultra-high vacuum chamber that maintains a basal pressure of $5\times10^{-11}$ torr. STM imaging and current-voltage measurements used commercially available Pt—Ir probes (Materials Analytic Services, Raleigh, N.C.). During obtaining the charge distribution of nanocomplex, the tip is scanned in constant-current mode according to the tunneling setpoint conditions (0.1 nA tunneling current and −1.2 V sample bias) until it reaches the indicated point for taking current-voltage measurements. At these predetermined points, the feedback of the tip position is held constant, and the sample bias is varied while the tunneling current is recorded. In this case, the threshold of the single detection for current is 10 pA when the same state at the surface is detected in the entire current range.

Figure 12:
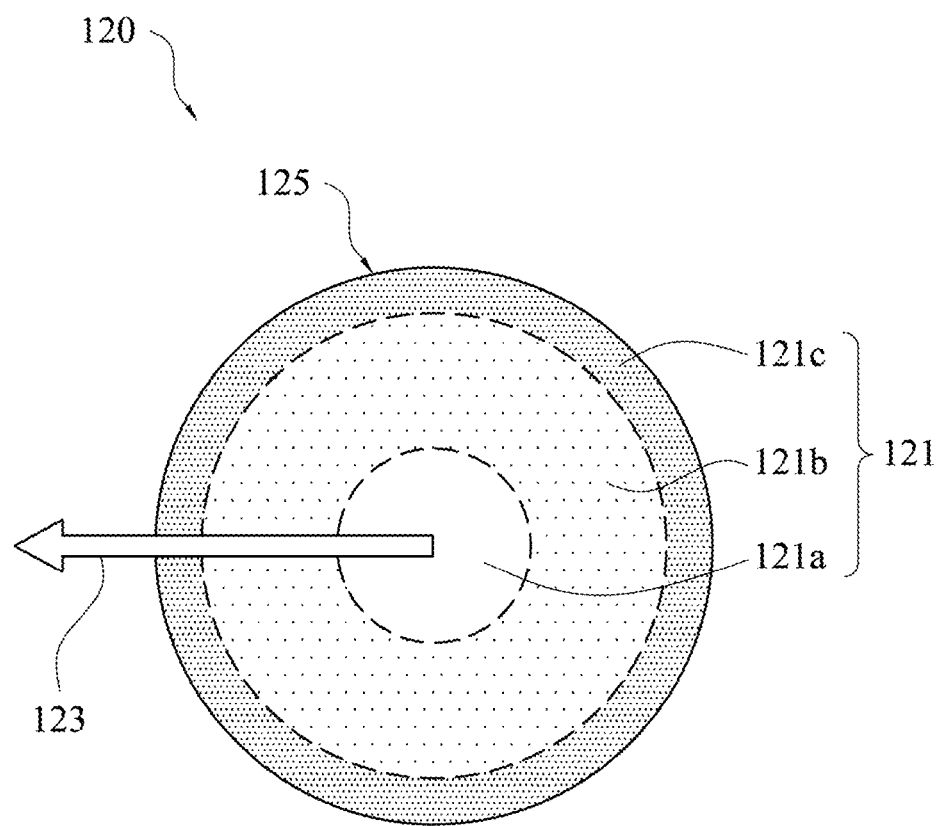
FIG. 12 shows a cross-sectional diagram of the nanocomplex of Sample 2 according to an embodiment of the present invention.

FIG. 11 showed images of molecular distributions (the images at the top row), the positively charge distributions (the images at the middle row) and the combined distributions (the images at the bottom row) of the nanocomplexes of Samples 1 to 3 of Example 8 according to some embodiments of the present invention. FIG. 12 showed a cross-sectional diagram of the nanocomplex of Sample 2 according to an embodiment of the present invention.

As shown in FIGS. 11 and 12, the nanocomplex 120 of Sample 2 had a nonuniformally and positively charge distribution 121 along a radial direction 123 thereof, the nonuniformally and positively charge distribution 121 of the nanocomplex of Sample 2 comprised a first electrically charged portion, 121a a second electrically charged portion 121b surrounding the first electrically charged portion 121a, and a third electrically charged portion 121c surrounding the second electrically charged portion 121b. The first electrically charged portion 121a had a first volume charge density being substantially neutral (being blank in the central region of the nanocomplex of Sample 2 at the top row of FIG. 11). The third electrically charged portion 121c includes an outermost surface 125 of the nanocomplex 120, and the third electrically charged portion 121c has a third volume charge density (exhibiting a darker green color near the outermost surface of the nanocomplex of Sample 2 at the middle row of FIG. 11) more than a second volume charge density (exhibiting a lighter green color between the outermost surface and the central region of the nanocomplex of Sample 2 at the middle row of FIG. 11) of the second electrically charged portion 121b.

Figure 13A:
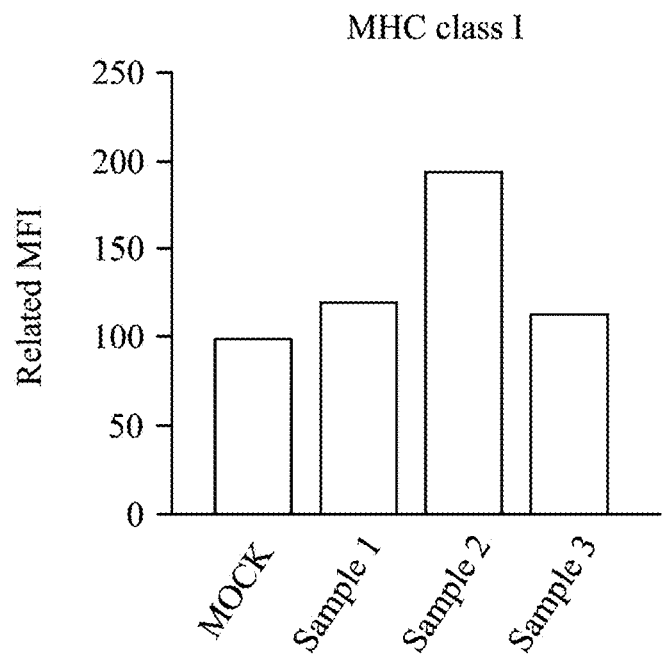
FIGS. 13A and 13B shows relative levels of antibodies to MHC class I (FIG. 13A) and MHC class II (FIG. 13B) of mice administrated with the nanocomplexes of Samples 1 to 3 of Example 8 according to embodiments of the present invention.
Figure 13B:
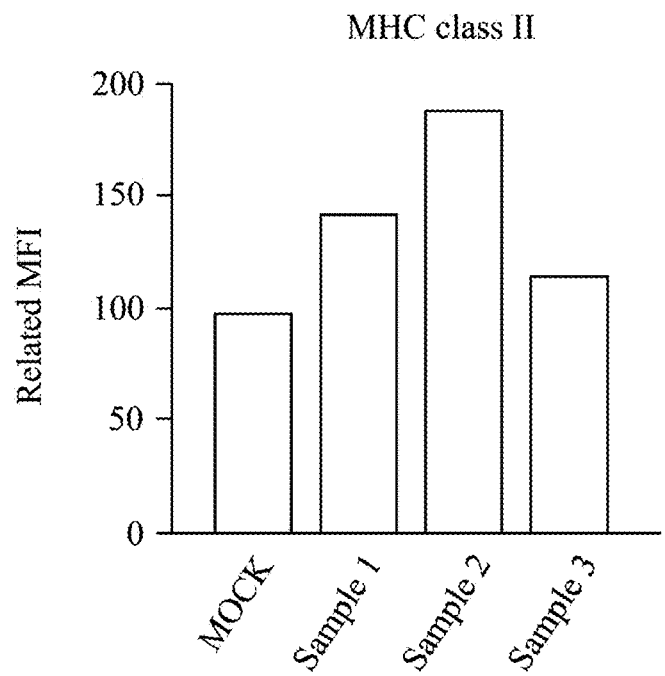

Reference was made to FIGS. 13A and 13B, which showed relative levels (mean fluorescence intensity; MFI) of antibodies to MHC class I (FIG. 13A) and MHC class II (FIG. 13B) of mice administrated with the nanocomplexes of Samples 1 to 3 of Example 8 according to embodiments of the present invention.

As shown in FIGS. 13A and 13B, the nanocomplex of Sample 2 had a higher antibody titer and higher levels of antibodies to MHC class I and MHC class II, exhibiting an better enhancement of CD8(+) T-cell response than the nanocomplexes of Samples 1 and 3.

The present invention developed a polymeric particle-based adjuvant to actively immunize mice with DJ NS1 protein and to evaluate its protective effects in a DENV-infected mouse model. After two rounds of immunization, a superior Ab response induced by DJ NS1-encapsulated nanocomplexes was observed, as compared to DJ NS1 with alum. The detailed mechanisms of how DJ NS1-encapsulated nanocomplexes induce higher and long-lasting Ab titers were, however, still unclear. It has been reported that nanoparticle sizes between 200 to 600 nm are efficiently taken up by APCs. Phagocytosis occurs more efficiently if vesicles are positively charged and spherical or cylindrical in shape compared with negatively charged or disk-shaped particles. The nanoparticles used in the present invention were positively charged with a spherical shape and a diameter of ~280 nm.

The superior adjuvant properties of nanocomplexes over alum were clearly evident from our present study. The underlying mechanisms are not certain, but likely involve a depot effect resulting from the particulate DJ NS1 nanocomplexes at the skin inoculation site. For example, liposomes as adjuvant can form an antigen depot at the site of injection and induce immunological recall responses. In contrast, alum has been reported to fail to sustain antigen availability in draining lymph nodes and likely does not contribute to an antigen depot effect in its adjuvant activity. Further studies are required to validate this and to determine the levels and locations of DJ NS1-encapsulated nanocomplexes processed by antigen-presenting cells, such as macrophages and DCs.

A requirement of a dengue vaccine is that the immunity elicited by the vaccine should provide long-term protection. Therefore, the levels of NS1-specific Abs in mouse sera were determined every week after immunization. It was found that the Ab titers induced by DJ NS1-encapsulated nanocomplexes remained detectable till 18-19 weeks, whereas the Ab titers induced by DJ NS1 plus alum could be detected only up to 8 weeks after immunization. Moreover, at 21 weeks when the serum Ab titer was no longer detectable, mice inoculated with DJ NS1-encapsulated nanocomplexes produced anti-DJ NS1 IgG titers of $2^6$ ($\times10^3$) at 3 days post-infection. These data suggest that DJ NS1-encapsulated nanocomplexes can induce effective Ab responses and provide long-term protection in this DENV-infected mouse model.

Besides the efficient Ab responses, the question as to whether DJ NS1-encapsulated nanocomplexes can induce a CD8$^+$ T cell response is of interest for further investigation. In a previous study examining dengue-specific T cells from 18 dengue fever patients and 22 DHF patients, it was found that CD8$^+$ T cells mainly recognized the NS3 and NS5 proteins. However, two human CD8$^+$ T cell epitopes have been identified in the DENV4 NS1 protein. After immunization of mice with these epitope-containing peptides, DENV4 specific CD8$^+$ T cells were activated. It also remains to be determined whether the DJ NS1-encapsulated nanocomplexes can induce cross-presentation of exogenous antigen by DCs. A previous study using γ-PGA as adjuvant showed enhanced endoplasmic reticulum (ER)-endosome fusion and translocation of the confined ovalbumin antigens from the fused ER-endosome complex to the cytosol via ER-translocon sec61. Subsequently, the released antigens were degraded by cytoplasmic proteasomes and transported to the ER via TAP, followed by presentation of the antigen-MHC class I complex on the cell surface.

Previous studies showed that macrophages produce different patterns of cytokines and direct the immune response towards a Th1 or Th2 phenotype by responding to the endocytosis of large or small lipid vesicles[43]. Recent reports demonstrated that particle-based adjuvants can facilitate antigen cross-presentation to activate $CD8^+$ T cells. However, it still remains unclear as to whether nanocomplexes as adjuvant will induce a Th1, Th2, or mixed Th1/Th2 response. The DJ NS1-specific IgG2a and IgG1 Abs were determined for Th1 and Th2 responses, respectively, in mouse sera. The results showed that DJ NS1-encapsulated nanocomplexes can induce both Th1/Th2 responses, while DJ NS1 plus alum mainly induced a Th2 response. A previous study indicated that chitosan could enhance antigen-specific splenic $CD4^+$ T cell proliferation and induce a mixed Th1/Th2 response in mice. However, g-PGA-stimulated DCs favored the polarization of naïve $CD4^+$ T cells towards a Th1 phenotype. The cytokine patterns were further confirmed in mouse sera showing higher Th1 cytokine levels induced by DJ NS1-encapsulated nanocomplexes as compared with DJ NS1 plus alum. Conversely, Th2 cytokine levels were lower in the DJ NS1-encapsulated nanocomplexes group than in the DJ NS1 plus alum-treated group. In summary with DJ NS1 as antigen, nanocomplexes as adjuvant induce both Th1 and Th2 responses, but the detailed mechanisms need to be further investigated.

Several dengue vaccine candidates are in clinical trials, mostly chimeric live vaccines and live attenuated vaccines. Other candidates like subunit vaccines (envelope and NS1 proteins), whole inactive virus vaccines, and DNA vaccines are also under development. Increasing interest has focused on the NS1 as a candidate for therapeutic strategies including vaccine development. In addition to targeting cell-surface NS1 to trigger complement-mediated lysis of DENV-infected cells, a recent study showed that NS1 may trigger endothelial permeability and vascular leakage, suggesting that NS1 may be a new potential target for dengue therapeutics and vaccines. Immunization of mice with NS1 from DENV1 to DENV4 provided protection against DENV challenge[60]. The contribution of NS1 to vascular leakage was further supported by the finding that NS1 activates cells via TLR4 and, moreover, disrupts endothelial cell monolayer integrity. Meanwhile, another study showed that NS1 may also activate cells via TLR2 and TLR6.

Ensuring cross-protection against the four different serotypes of DENV is an important issue for dengue vaccine development. Whether NS1-encapsulated polymer-based nanocomplexes can provide serotypic cross-protection needs to be determined. Besides the C-terminal region of NS1, another group found that a.a. 116-119 also showed cross-reactivity to endothelial cell autoantigen LYRIC. Therefore, additional cross-reactive regions of NS1 may also need to be considered for their potential harmful effects in NS1-based vaccine development.

In conclusion, the present study shows that active immunization with DJ NS1-encapsulated nanocomplexes can induce effective immune responses and provide protection against DENV infection. Importantly, DJ NS1-encapsulated nanocomplexes provide long-term protection in the mouse model. As compared with alum as an adjuvant, DJ NS1-encapsulated nanocomplexes possess at least three advantages: 1) inducing higher Ab titers; 2) inducing long-lasting Ab titers; and 3) inducing balanced Th1/Th2 responses. A safe and efficient vaccine against DENV should ideally focus on inducing both T cell and antibody responses. Alum is the most common adjuvant used in approved vaccines due to its safety profile and ability to enhance protective humoral immune responses. However, alum mainly stimulates a Th2 response which makes it unsuitable for certain vaccines. Therefore, DJ NS1-encapsulated nanocomplexes can induce a mixed Th1/Th2 response.

Although the present invention has been described in considerable detail with reference to certain embodiments thereof, other embodiments are possible. It is necessarily supplemented that, specific dengue viral protein, specific components, specific manufacturing process, specific experimental animals, specific analysis methods or specific apparatuses are employed as exemplary embodiments for clarifying the immunostimulatory nanocomplex and the method for making the same of the present invention. However, as is understood by a person skilled in the art, other proteins, other components, other manufacturing process, other experimental animals, other analysis methods or other apparatuses can be also employed in the immunostimulatory nanocomplex and the method for making the same of the present invention, rather than being limited thereto.

According to the above description, in comparison with the traditional technique, the immunogenic composition, the method for making a biodegradable nanocomplex using the immunogenic composition, and the vaccine composition comprising the biodegradable nanocomplex according to the present invention has the advantages as following:

1. The immunostimulatory nanocomplex of the present invention can induce a specific antibody response to the dengue viral protein in mice after administration twice. In comparison with the Alum adjuvant and Ribi adjuvant used in the traditional dengue vaccine of the prior art, the administration times of the biodegradable high-efficiency dengue vaccine in the present invention is decreased to further reduce the administration cost, so the immunostimulatory nanocomplex is good for being a commercial vaccine.
2. After administration with the vaccine composition of the present invention twice, the organism has the antibody titer of 32000 at least. In comparison with the prior art, the vaccine composition of the present invention substantially increases the antibody production to induce the immune response efficiently for enhancing the protection effect of the vaccine composition.
3. The biodegradable nanocomplex of the vaccine composition of the present invention is made from the mixture of the biodegradable polyglutamic acid (or heparin) and chitosan to hold the dengue viral protein inside. Accordingly, the dengue vaccine is decomposed, absorbed and removed easily and naturally by the human body after it enters the human body. It resolves the unsafe problems resulting from the heavy metal of the Alum adjuvant, and the dengue viral protein held in the nanocomplex is released slowly for the sustained release.

According to the embodiments of the present invention, the aforementioned immunogenic composition, the method for making a biodegradable nanocomplex using the immunogenic composition, and the vaccine composition comprising the biodegradable nanocomplex, a desired biodegradable nanocomplex with the adjustable zeta potential and the desired particle size can be easily produced, for saving the testing numbers, obtaining the biodegradable nanocomplex with more uniform diameter and less standard deviation, and providing better administration effect to an organism.

Although the present invention has been described in considerable detail with reference to certain embodiments thereof, other embodiments are possible. Therefore, the spirit and scope of the appended claims should not be limited to the description of the embodiments contained herein.

What is claimed is:

1. An immunostimulatory nanocomplex comprising polyglutamic acid (PGA), a first positively charged substance, a second positively charged substance and a dengue viral protein, wherein the dengue viral protein is held inside the immunostimulatory nanocomplex, wherein the immunostimulatory nanocomplex has a nonuniform positive charge distribution along a radial direction thereof, and the nonuniform positive charge distribution comprises: a first electrically charged portion having a first volume charge density that is substantially neutral; a second electrically charged portion surrounding the first electrically charged portion; and a third electrically charged portion surrounding the second electrically charged portion, wherein the third electrically charged portion has a third volume charge density higher than a second volume charge density of the second electrically charged portion, and the third electrically charged portion comprises an outermost surface of the immunostimulatory nanocomplex.

2. The immunostimulatory nanocomplex according to claim 1, wherein the immunostimulatory nanocomplex has a zeta potential of 10 mV to 35 mV.

3. The immunostimulatory nanocomplex according to claim 1, wherein the first positively charged substance and the second positively charged substance are the same.

4. The immunostimulatory nanocomplex according to claim 1, wherein the first positively charged substance and the second positively charged substance are selected from the group consisting of chitosan (CS), gelatin, cationic cyclodextrin, cationic dextran, poly(L-lysine), polyethylenimine, and polyamidoamine.

5. The immunostimulatory nanocomplex according to claim 1, wherein the dengue viral protein comprises the sequence of SEQ ID NO 1 or 2.

* * * * *

SEQUENCE LISTING

```
<160> NUMBER OF SEQ ID NOS: 2

<210> SEQ ID NO 1
<211> LENGTH: 352
<212> TYPE: PRT
<213> ORGANISM: Artificial Sequence
<220> FEATURE:
<223> OTHER INFORMATION: Recombinant protein of Dengue virus and
      Japanese encephalitis virus

<400> SEQUENCE: 1

Asp Ser Gly Cys Val Val Ser Trp Lys Asn Lys Glu Leu Lys Cys Gly
  1               5                  10                  15

Ser Gly Ile Phe Ile Thr Asp Asn Val His Thr Trp Thr Glu Gln Tyr
             20                  25                  30

Lys Phe Gln Pro Glu Ser Pro Ser Lys Leu Ala Ser Ala Ile Gln Lys
         35                  40                  45

Ala His Glu Glu Gly Ile Cys Gly Ile Arg Ser Val Thr Arg Leu Glu
     50                  55                  60

Asn Leu Met Trp Lys Gln Ile Thr Pro Glu Leu Asn His Ile Leu Ser
 65                  70                  75                  80

Glu Asn Glu Val Lys Leu Thr Ile Met Thr Gly Asp Ile Lys Gly Ile
                 85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Pro Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Arg Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Ser Cys His
    210                 215                 220

Trp Pro Lys Pro His Thr Leu Trp Ser Asn Gly Val Leu Glu Ser Glu
225                 230                 235                 240

Met Ile Ile Pro Lys Asn Phe Ala Gly Pro Val Ser Gln His Asn Tyr
                245                 250                 255

Arg Pro Gly Tyr His Thr Gln Thr Ala Gly Pro Trp His Leu Gly Lys
            260                 265                 270

Leu Glu Met Asp Phe Asp Phe Cys Glu Gly Thr Thr Val Val Val Thr
        275                 280                 285

Glu Asp Cys Gly Asp Arg Gly Pro Ser Leu Arg Thr Thr Thr Ala Ser
    290                 295                 300

Gly Lys Leu Ile Thr Glu Trp Cys Cys Arg Ser Cys Thr Leu Pro Pro
305                 310                 315                 320
```

```
Leu Arg Tyr Arg Gly Glu Asp Gly Cys Trp Tyr Gly Met Glu Ile Arg
                325                 330                 335

Pro Leu Lys Glu Lys Glu Asn Leu Val Asn Ser Leu Val Thr Ala
                340                 345                 350

<210> SEQ ID NO 2
<211> LENGTH: 270
<212> TYPE: PRT
<213> ORGANISM: Artificial Sequence
<220> FEATURE:
<223> OTHER INFORMATION: Recombinant protein of Dengue virus

<400> SEQUENCE: 2

Asp Ser Gly Cys Val Val Ser Trp Lys Asn Lys Glu Leu Lys Cys Gly
  1               5                  10                  15

Ser Gly Ile Phe Ile Thr Asp Asn Val His Thr Trp Thr Glu Gln Tyr
             20                  25                  30

Lys Phe Gln Pro Glu Ser Pro Ser Lys Leu Ala Ser Ala Ile Gln Lys
         35                  40                  45

Ala His Glu Glu Gly Ile Cys Gly Ile Arg Ser Val Thr Arg Leu Glu
     50                  55                  60

Asn Leu Met Trp Lys Gln Ile Thr Pro Glu Leu Asn His Ile Leu Ser
 65                  70                  75                  80

Glu Asn Glu Val Lys Leu Thr Ile Met Thr Gly Asp Ile Lys Gly Ile
                 85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Pro Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Arg Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Ser Cys His
    210                 215                 220

Trp Pro Lys Pro His Thr Leu Trp Ser Asn Gly Val Leu Glu Ser Glu
225                 230                 235                 240

Met Ile Ile Pro Lys Asn Phe Ala Gly Pro Val Ser Gln His Asn Tyr
                245                 250                 255

Arg Pro Gly Tyr His Thr Gln Thr Ala Gly Pro Trp His Leu
            260                 265                 270
```